(12) United States Patent
Amaral et al.

(10) Patent No.: US 7,604,948 B2
(45) Date of Patent: Oct. 20, 2009

(54) BIOMARKERS FOR DIAGNOSING AN AUTISM SPECTRUM DISORDER

(75) Inventors: David G. Amaral, Davis, CA (US); Blythe A. Corbett, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 285 days.

(21) Appl. No.: 11/381,976

(22) Filed: May 5, 2006

(65) Prior Publication Data

US 2007/0003922 A1 Jan. 4, 2007

Related U.S. Application Data

(60) Provisional application No. 60/678,865, filed on May 5, 2005.

(51) Int. Cl.
*G01N 33/53* (2006.01)
*G01N 33/542* (2006.01)
*G01N 33/537* (2006.01)
*G01N 33/543* (2006.01)
*G01N 33/566* (2006.01)
*G01N 33/567* (2006.01)
*G01N 33/561* (2006.01)
*G01N 33/536* (2006.01)
*G01N 24/00* (2006.01)

(52) U.S. Cl. .................. 435/7.1; 435/7.8; 435/7.9; 435/7.92; 435/7.94; 436/501; 436/503; 436/516; 436/536; 436/173

(58) Field of Classification Search ...................... None
See application file for complete search history.

(56) References Cited

U.S. PATENT DOCUMENTS

2004/0091943 A1  5/2004  Schneider

OTHER PUBLICATIONS

Spence et al., 2004, Semin. Pediatr. Neurol., 11, pp. 186-195.*
Zipfel et al., 2002, Biochem Soc. Transactions, 30, pp. 971-978.*
Raitanen et al., 1999, Scan. J. Urol. Nephrol., 33, pp. 234-236.*
Donahue et al., 2004, Circulation, 110, No. 17, Suppl. III, 1011.*
Corbett, et al., "A Proteomic Study of Serum From Children With Autism Showing Differential Expression of Apolipoproteins and Complement Proteins," *Molecular Psychiatry*, (2007) 12, 292-306.
Ashwood, P., et al., "Spontaneous mucosal lymphocyte cytokine profiles in children with autism and gastrointestinal symptoms: mucosal immune activation and reduced counter regulatory interleukin-10," *J Clin Immunol*, 24(6), 664-673 (2004).
Ashwood, P., et al., "A review of autism and the immune response," *Clinical and Developmental Immunology*, vol. 11(2), 165-174 (Jun. 2004).
Ashwood, P., et al., "Is autism an autoimmune disease?" *Autoimmune Rev.*, vol. 3(7-8), 13 pgs. (Nov. 2004).

Cantor, R., et al., "Replication of autism linkage: fine-mapping peak at 17q21," *Am J Hum Genet*, 76(6), 1050-1056 (2005).
Croen, L., et al., "Maternal autoimmune diseases, asthma and allergies, and childhood autism spectrum disorders," *Arch. Pediatr. Adolesc Med.*, vol. 159, 151-157 (Feb. 2005).
DeFelice, M., et al., "Intestinal cytokines in children with pervasive developmental disorders," *Am J Gastroenterol.*, 98(8), 1777-1782 (2003).
Ferrante, P., et al., "Significant association of HLA A2-DR11 with CD4 naive decrease in autistic children," *Biomed Pharmacother.*, 57(8), 372-374 (2003).
Geschwind, D., et al., "The autism genetic resource exchange: a resource for the study of autism and related neuropsychiatric conditions," *Am J Hum Genet.*, 69(2), 463-466 (2001).
Jyonouchi, H., et al., "Evaluation of an association between gastrointestinal symptoms and cytokine production against common dietary proteins in children with autism spectrum disorders," *J Pediatr.*, 146(5), 605-610 (2005).
Jyonouchi, H., et al., "Innate immunity associated with inflammatory responses and cytokine production against common dietary proteins in patients with autism spectrum disorder," *Neuropsychobiology.*, 46(2), 76-84 (2002).
Jyonouchi, H., et al., "Proinflammatory and regulatory cytokine production associated with innate and adaptive immune responses in children with autism spectrum disorders and developmental regression," *J Neuroimmunol.*, 120(1-2), 170-179 (2001).
McCauley, J., et al., "Genome-wide and Ordered-Subset linkage analyses provide support for autism loci on 17q and 19p with evidence of phenotypic and interlocus genetic correlates," *BMC Med Genet.*, 6, 1 (2005).
Molloy, C., et al., "Elevated cytokine levels in children with autism spectrum disorder," *J Neuroimmunol*, 14 (2005).
Odell, D., et al., "Confirmation of the association of the C4B null allelle in autism," *Hum Immunol.*, 66(2), 140-145 (2005).
Purcell, A., et al., "The abnormal regulation of gene expression in autistic brain tissue," *J Autism Dev Disord*, 31(6), 545-549 (2001).
Risch, N., "Searching for genetic determinants in the new millennium," *Nature*, 405(6788), 847-856 (2000).
Risch, N., et al., "A genomic screen of autism: evidence for a multilocus etiology," *Am J Hum Genet*, 65(2), 493-507 (1999).
Segurado, R., et al., "Confirmation of Association Between Autism and the Mitochondrial Aspartate/Glutamate Carrier SLC25A12 Gene on Chromosome 2q31," *Am J Psychaiatry*, 162(11), 2182-2184 (2005).

(Continued)

*Primary Examiner*—Olga N Chernyshev
(74) *Attorney, Agent, or Firm*—Townsend and Townsend and Crew LLP

(57) ABSTRACT

The present invention provides methods of identifying biomarkers indicative of the presence of a neurodevelopmental disorder, including an autism spectrum disorder, in an individual, using cytometry and mass spectrometry. The invention further provides methods of using the identified biomarkers to diagnose the presence of a neurodevelopmental disorder, including an autism spectrum disorder.

15 Claims, 23 Drawing Sheets

OTHER PUBLICATIONS

Singh, V., "Plasma increase of interleukin-12 and interferon-gamma. Pathological significance in autism," *J Neuroimmunol.*, 66(1-2), 143-145 (1996).

Singh, et al., "Prevalence of serum antibodies to caudate nucleus in autistic children," *Neuroscience Letters*, vol. 355, 53-56 (2004).

Torres, A., et al., "The association of MHC genes with autism," *Front Biosci*, 6, D936-943 (2001).

Torres, A., et al., "The transmission disequilibrium test suggests that HLA-DR4 and DR13 are linked to austism spectrum disorder," *Hum Immunol.*, 63(4), 311-316 (2002).

Torres, A., et al., " Is fever suppression involved in the etiology of autism and neurodevelopmental disorders?" *BMC Pediatrics*, vol. 3(9), pp. 1-6 (2003).

Vargas, D., et al., "Neuroglial activation and neuroinflammation in the brain of patients with autism," *Ann. Neurol.*, vol. 57, 67-81 (2005).

Vorstman, J., et al., "Identification of novel autism candidate regions through analysis of reported cytogenetic abnormalities associated with autism," *Mol Psychiatry*, 4 (2005).

Van Gent, T., et al., "Autism and the immune system," *J Child Psychol Psychiatry*, 38(3), 337-349 (1997).

Warren, R., et al., "Strong association of the third hypervariable region of HLA-DR beta 1 with autism," *J Neuroimmunol.*, 67(2), 97-102 (1996).

Warren, R., et al., "Immunogenetic studies in autism and related disorders," *Mol Chem Neuropathol.*, 28(1-3), 77-81 (1996).

Warren, R., et al., "DR-positive T cells in autism: association with decreased plasma levels of the complement C4B protein," *Neuropsychobiology.*, 31(2), 53-57 (1995).

Wassink, T., et al., "The search for autism disease genes," *Ment Retard Dev Disabil Res Rev.*, 10(4), 272-283 (2004).

Zimmerman, A., et al., "Cerebrospinal fluid and serum markers of inflammation in autism," *Pediatr Neurol.*, 33(3), 195-201 (2005).

\* cited by examiner

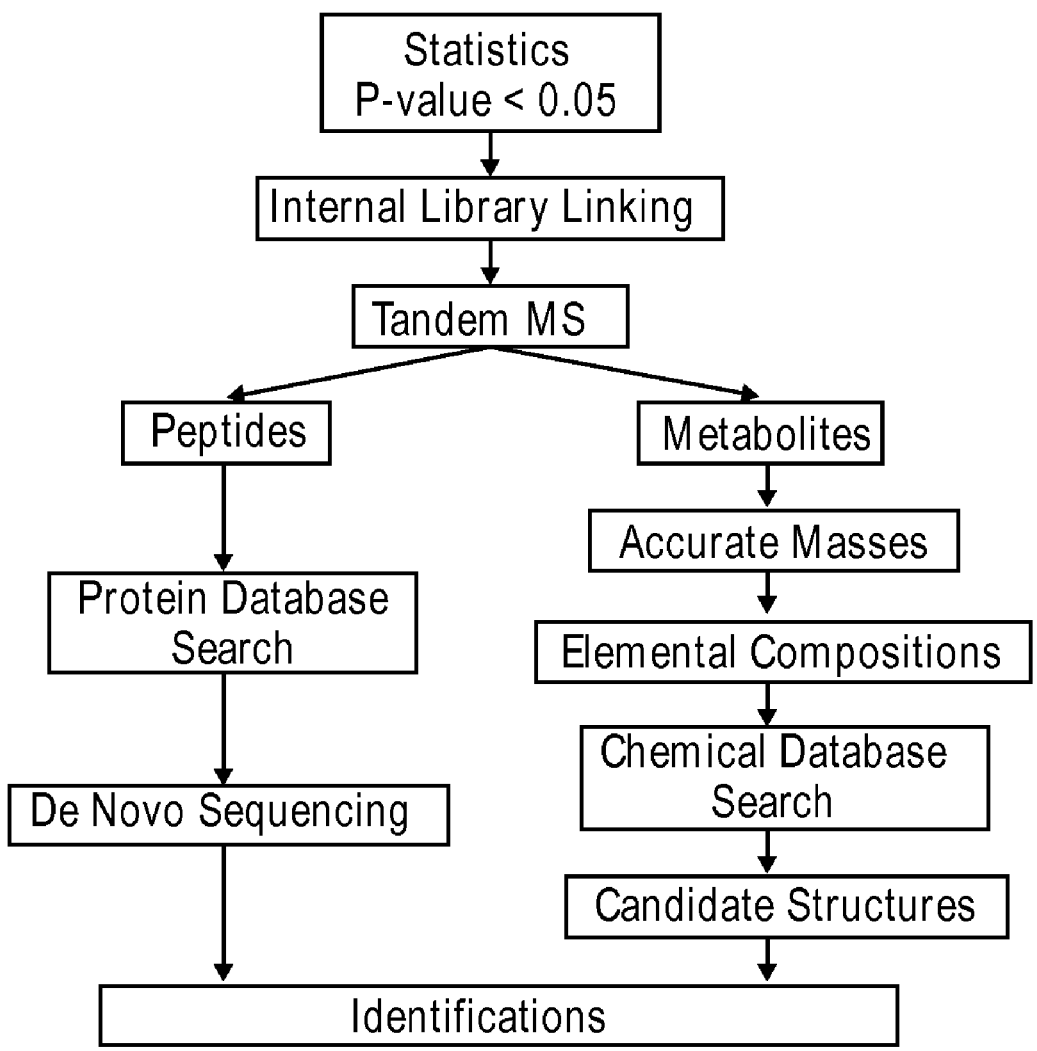

HLA-DR on CD8 T cells is 30-60% higher in children with Autism

HLA-DR on CD8 T cells is 30-60% higher in children with Autism

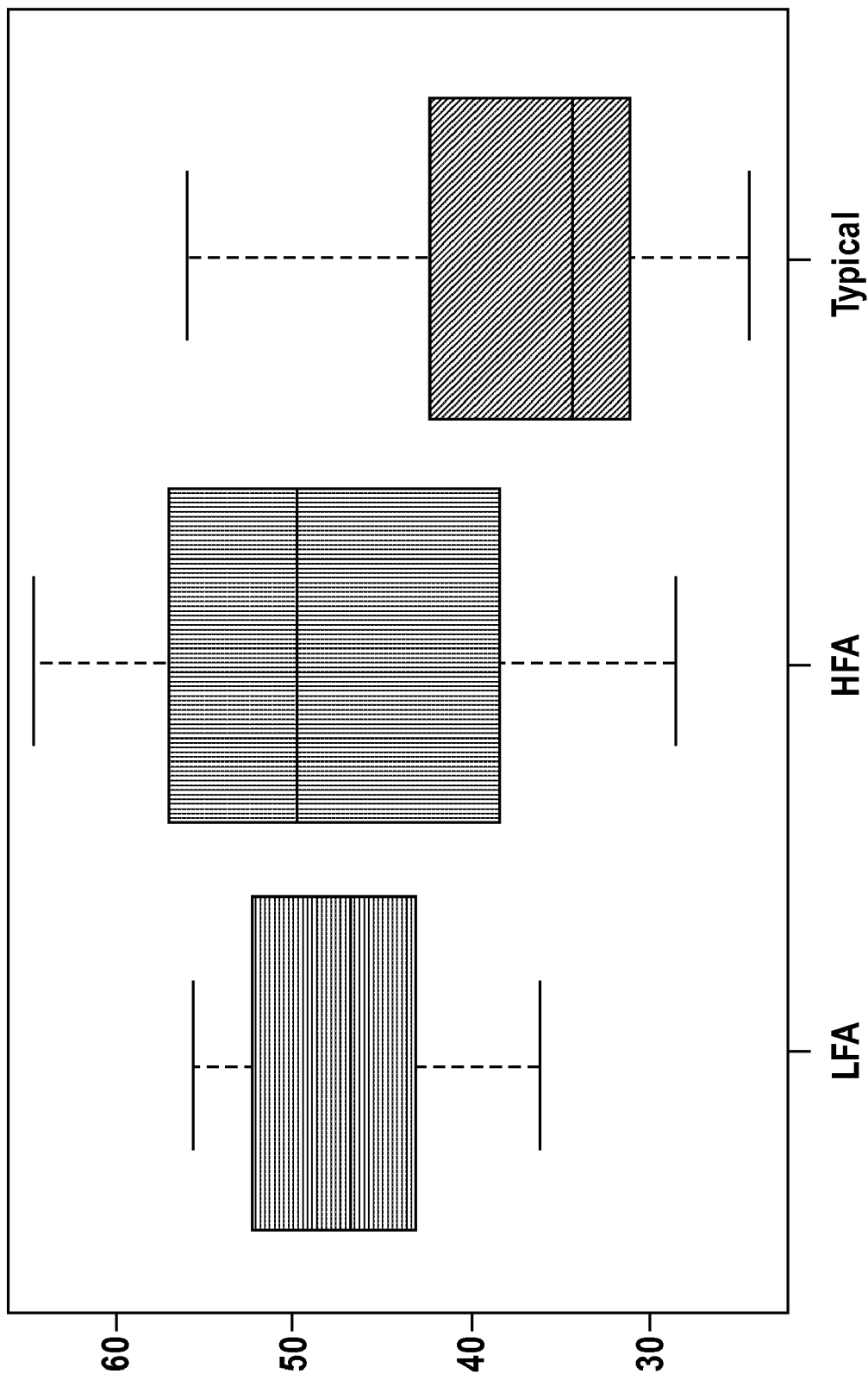

BIOMARKERS FOR DIAGNOSING AN AUTISM SPECTRUM DISORDER

CROSS REFERENCE TO RELATED APPLICATIONS

This application claims the benefit of U.S. Provisional Patent Application No. 60/678,865, filed May 5, 2005, the entire disclosure of which is hereby incorporated herein by reference.

FIELD OF THE INVENTION

The present invention is directed to methods for diagnosing neurodevelopmental disorders, including autism, by employing a multiplatform analysis of blood cell immunophenotype and serum polypeptide and metabolite content.

BACKGROUND OF THE INVENTION

Autism spectrum disorders (ASD) are a neurodevelopmental disorder characterized by impairments in reciprocal social interaction, deficits in verbal and nonverbal communication, and a restricted repertoire of activities or interests. There are currently no diagnostic tests for autism. Early identification of the susceptibility to autism of an individual would dramatically reduce or eliminate the severity of the condition by allowing for appropriate interventions.

Because there has been about a 5-fold increase in the diagnosis of new cases of autism spectrum disorder in the last decade in children aged 1.5-6 years, there remains an important need for a reliable diagnostic test to identify susceptibility to the development of an ASD. The present invention fulfills this and other needs.

BRIEF SUMMARY OF THE INVENTION

In one aspect, the present invention provides methods for identifying one or more immune cell markers indicative of a neurodevelopmental disorder, including an autism spectrum disorder, said method comprising:
(a) detecting a phenotypic profile of an immune cell population in a test sample from an individual having a neurodevelopmental disorder, including an autism spectrum disorder; and
(b) comparing the phenotypic profile of the immune cells in said immune cell population from said test sample to a phenotypic profile of a corresponding immune cell population in a control sample from an individual not having a neurodevelopmental disorder;
wherein said one or more immune cell markers indicative of a neurodevelopmental disorder is identified by a difference in the phenotypic profile of the immune cells in said immune cell population between said test sample and said control sample.

In a further aspect, the present invention provides methods for identifying one or more polypeptide markers indicative of a neurodevelopmental disorder, including an autism spectrum disorder, said method comprising:
(a) obtaining a mass spectrum of one or more polypeptides in a high molecular weight fraction from a test sample from an individual having a neurodevelopmental disorder, including an autism spectrum disorder; and
(b) comparing the mass spectrum from said test sample to a corresponding high molecular weight fraction mass spectrum from a control sample from an individual not having a neurodevelopmental disorder,
wherein said one or more polypeptide markers indicative of a neurodevelopmental disorder is identified by the presence or absence, or differential presence, of one or more polypeptides (proteins or peptides) between said test sample and said control sample.

In a further aspect, the present invention provides methods for identifying one or more metabolite markers indicative of a neurodevelopmental disorder, including an autism spectrum disorder, said method comprising:
(a) obtaining a mass spectrum of one or more metabolites in a low molecular weight fraction from a test sample from an individual having a neurodevelopmental disorder, including an autism spectrum disorder; and
(b) comparing the mass spectrum from said test sample to a corresponding low molecular weight fraction mass spectrum from a control sample from an individual not having a neurodevelopmental disorder,
wherein said one or more metabolite markers indicative of a neurodevelopmental disorder are identified by the presence or absence, or differential presence, of one or more metabolites between said test sample and said control sample.

In one aspect, the present invention provides methods for diagnosing the susceptibility to a neurodevelopmental disorder, including an autism spectrum disorder, in an individual, said method comprising:
determining the presence or absence, or differential presence, of one or more markers indicative of a neurodevelopmental disorder, including an autism spectrum disorder, in a sample from a first individual suspected of having a susceptibility to a neurodevelopmental disorder, the one or more markers selected from the group consisting of one or more immune cell markers, and one or more polypeptide markers, wherein the increased or decreased presence of said one or more markers in comparison to a sample from a second individual who does not have a neurodevelopmental disorder indicates that said first individual has a susceptibility to a neurodevelopmental disorder.

In a further aspect, the present invention provides methods for diagnosing the susceptibility to a neurodevelopmental disorder, including an autism spectrum disorder, in an individual, said method comprising:
determining the presence or absence, or differential presence, of one or more markers indicative of a neurodevelopmental disorder, including an autism spectrum disorder, in a sample from a first individual suspected of having a susceptibility to a neurodevelopmental disorder, the one or more markers selected from the group consisting of one or more immune cell markers, one or more polypeptide markers, and one or more metabolite markers, wherein the increased or decreased presence of said one or more markers in comparison to a sample from a second individual who does not have a neurodevelopmental disorder indicates that said first individual has a susceptibility to a neurodevelopmental disorder.

In a further aspect, the present invention provides methods for distinguishing high functioning autism from low functioning autism, the method comprising:
determining the comparative presence of one or more markers indicative of an autism spectrum disorder in a sample from an individual suspected of having an autism spectrum disorder, the one or more markers selected from the group consisting of one or more immune cell markers, one or more polypeptide markers, and one or more metabolite markers to control samples containing one or more markers known to be indicative of high functioning autism or low functioning autism.

Definitions

As used herein, the terms "proteome" or "proteomic" interchangeably refer to the population of polypeptides present in an biological sample from an individual at a particular time and under specific conditions.

The terms "metabolome" or "metabolomic" interchangeably refer to the population of metabolites (i.e., polypeptides, lipids, carbohydrates, nucleic acids, small organic molecules) present in an biological sample from an individual at a particular time and under specific conditions.

The term "neurodevelopmental disorder" refers to any condition, disease, disorder characterized by abnormal neurodevelopment and/or basic biobehavioral processes, including attentional and perceptual processing, executive function, inhibitory control (e.g., sensory gating), social cognition, and communication and affiliative behaviors. Exemplified neurodevelopmental disorders include attention deficit hyperactivity disorder, schizophrenia, obsessive-compulsive disorder, mental retardation, autistic spectrum disorders, cerebral palsy, articulation disorder, and learning disabilities (i.e., reading or arithmetic), verbal or performance aptitude. Further information on neurodevelopmental disorders can be found, for example, through the Neurodevelopmental Disorders Branch of the National Institute of Mental Health (worldwide website address at nihm.nih.gov/dptr/b2-nd.cfm). Additional information on neurodevelopmental disorders can be found, for example, in *Developmental Disabilities in Infancy and Childhood: Neurodevelopmental Diagnosis and Treatment*, Capute and Accardo, eds. 1996, Paul H Brookes Pub Co.; Hagerman, *Neurodevelopmental Disorders: Diagnosis and Treatment,* 1999, Oxford Univ Press; *Handbook of Neurodevelopmental and Genetic Disorders in Children*, Goldstein and Reynolds, eds., 1999, Guilford Press; *Handbook of Neurodevelopmental and Genetic Disorders in Adults*, Reynolds and Goldstein, eds., 2005, Guilford Press; and *Neurodevelopmental Disorders*, Tager-Flusberg, ed., 1999, MIT Press.

The term "autism spectrum disorder" or "autistic spectrum disorder" interchangeably refer to a spectrum of neurodevelopmental disorders characterized by impaired social interaction and communication accompanied by repetitive and stereotyped behavior. Autism includes a spectrum of impaired social interaction and communication, however, the disorder can be roughly categorized into "high functioning autism" or "low functioning autism," depending on the extent of social interaction and communication impairment. Individuals diagnosed with "high functioning autism" have minimal but identifiable social interaction and communication impairments (i.e., Asperger's syndrome). Additional information on autism spectrum disorders can be found in, for example, *Autism Spectrum Disorders: A Research Review for Practitioners*, Ozonoff, et al., eds., 2003, American Psychiatric Pub; Gupta, *Autistic Spectrum Disorders in Children,* 2004, Marcel Dekker Inc; and Hollander, *Autism Spectrum Disorders,* 2003, Marcel Dekker Inc.

BRIEF DESCRIPTION OF THE DRAWINGS

FIG. 2. Schematic of the workflow in metabolite identification process. The first step after determining the statistics for differential expression—database library linking—is a matching process to molecules.

FIG. 20. Complement factor H-related protein peptide is higher in children with Autism. Complement factor H-related protein 1 precursor concentrations in children with low functioning autism (LFA (horizontal lines )) and high functioning autism (HFA (vertical lines)) compared to typical developing, normal children (Typical (diagonal lines)). The peptide sequence used to identify this protein, the Accession Number, p value and effect size are given in Table 17. Peptide=ITCTEEGWSPTPK (SEQ ID NO:5).

DETAILED DESCRIPTION

General

Figure 1:
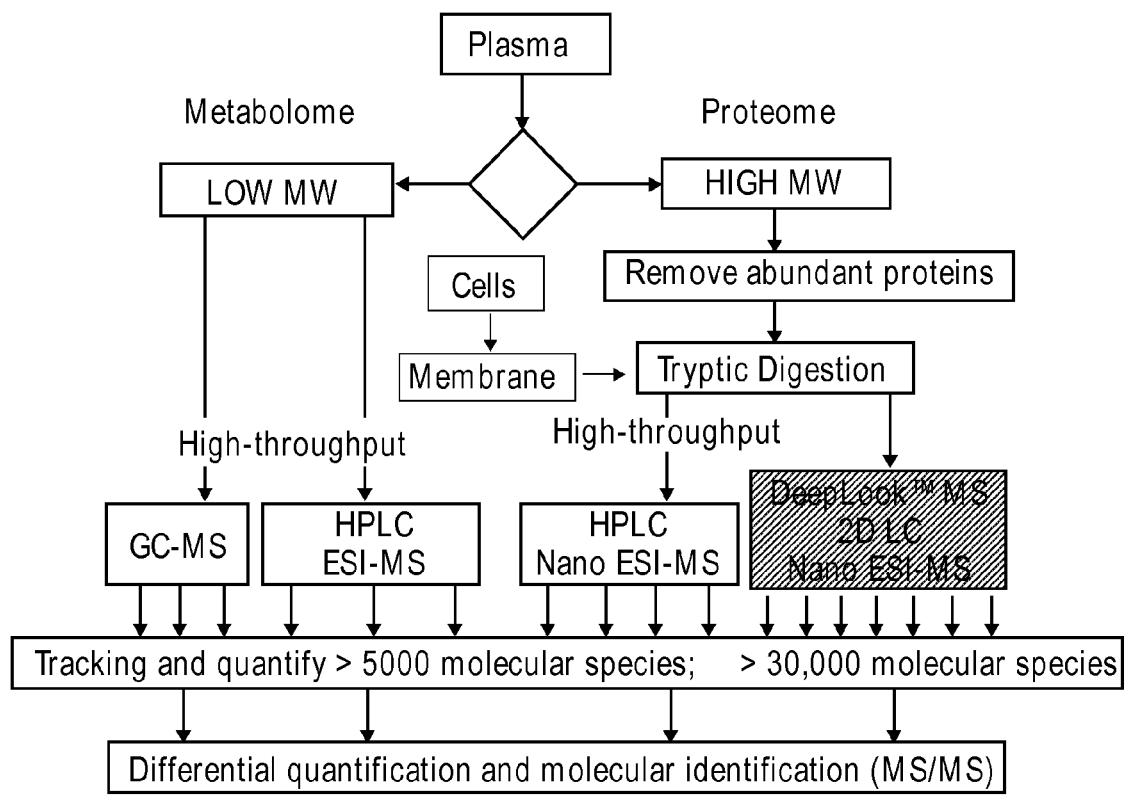
FIG. 1. Schematic diagram detailing the fractionation and mass spectrometric analysis used in this present study. This study used plasma as the starting material. Not used, but applicable to the present multiplatform methods is a Deep-Look™ analysis (SurroMed, LLC), a 2-dimensional separation of tryptic peptides that uses a first step of off-line strong-cation-exchange (SCX) chromatography and then on-line reverse-phase chromatography.

Autism can not currently be detected using standard diagnostic tests. The present invention provides methods and kits for diagnosing the presence or risk of a neurodevelopmental disorder, including an autism spectrum disorder, by determining one or more of an immunophenotypic profile of blood cells, a proteomic profile from a serum or blood sample, and a metabolomic profile from a serum or blood sample.

DETAILED EMBODIMENTS

Methods of Identifying Markers

In one aspect, the present invention provides methods for identifying one or more immune cell markers indicative of a neurodevelopmental disorder, including an autism spectrum disorder, said method comprising:
(a) detecting a phenotypic profile of an immune cell population in a test sample from an individual having a neurodevelopmental disorder, including an autism spectrum disorder; and
(b) comparing the phenotypic profile of the immune cells in said immune cell population from said test sample to a phenotypic profile of a corresponding immune cell population in a control sample from an individual not having a neurodevelopmental disorder;
wherein said one or more immune cell markers indicative of a neurodevelopmental disorder is identified by a difference in the phenotypic profile of the immune cells in said immune cell population between said test sample and said control sample.

In carrying out methods of identifying one or more immune cell markers indicative of a neurodevelopmental disorder, the presence or absence, or differential presence, of one or more immune cell surface markers of immune cell types and immune cell subtypes are identified using flow cytometry techniques well known to those in the art. See, for example, *Flow Cytometry Protocols*, Hawley and Hawley, eds., 2004, Human Press; Nunez, *Flow Cytometry for Research Scientists: Principles and Applications,* 2001, Springer Verlag; *Flow Cytometry for Biotechnology*, Sklar, ed., 2005, Oxford Univ. Press; and *Flow Cytometry in Clinical Diagnosis*, Keren, et al., eds., 2001, ASCP Press.

A presence or absence, or differential presence, can be demonstrated, for example, by a differential intensity of staining of one or more markers (i.e., increased or decreased cell surface expression), or by a differential cell counts (i.e., increased or decreased numbers of cells). A presence or absence, or differential presence, can be determined by visual inspection. Usually, a presence or absence, or differential presence, is determined by an analysis of quantified signals (i.e., intensity or cell number) of an identified immune cell population by a flow cytometer. Typically, the quantified signals of one or more immune cell markers are compared between two or more samples from individuals and a determination of a statistical difference between the samples is carried out. A presence or absence, or differential presence, also can be determined without statistical analysis. A differential presence (either increased or decreased) of one or more immune cell markers is identified when one sample gives a quantifiable signal that is, for example, 10%, 20%, 30%, 40%, 50%, 75%, 1-fold, 2-fold, 3-fold, 4-fold different from the one or more other samples being tested (i.e., a control or a sample from an individual with a different neurodevelopmental disorder).

An immune cell population from a sample of an individual being tested is contacted with one or more primary antibodies against cell surface proteins that identify particular immune cell types, for example, T cells (CD2, CD3, CD5, CD4 and CD8), B cells (CD19, CD20), NK cells (CD56, NKB1), granulocytes/eosinophils (CD15, CD16), monocytes (CD14), platelets (CD41a, CD45). Subtypes of T cells are identified with antibodies against cell surface markers including CD7, CD25, CD26, CD27, CD28, CD29, CD38, CD44 CD45RA, CD49d, CD54, CD57, CD60, CD62L, CD69, CD71, CD86, CD89, CD94, CD95, CD101, CD127, CD150, CD161, TCRαβ, TCRγδ, and CCR5. Subtypes of B cells are identified with antibodies against cell surface markers including CD5, CD27, CD38, CD40, CD44, CD62L, CD69, CD71, CD80, CD86, CD95, HLA-DP, HLA-DQ, HLA-DR, and PAN. Subtypes of NK cells are identified with antibodies against cell surface markers including CD2, CD7, CD8, CD57 and CD94. Subtypes of granulocyte/eosinophil cells are identified with antibodies against cell surface markers including CD11b, CD18, CD32, CD44, CD49d, CD52, CD64, CD66b, CD89, CD101, CD123, and IgED2. Subtypes of monocyte cells are identified with antibodies against cell surface markers including CD4, CD33, CD11b, CD38, CD44, CD54, CD60, CD62L, CD86, CD89, CD95, CD101, CD119, CD150, HLA-DP, HLA-DQ, HLA-DR, PAN, toll-like receptor-2 (TLR2), and TLR4. Subtypes of platelets are identified with antibodies against cell surface markers including CD62P and MOPC. Additional CD antigens are reviewed, for example, in Janeway, et al., *Immunobiology*, 2001, Garland Publishing; and Mason, et al., *Tissue Antigens* (2001) 58:425. Antibodies against immune cell surface markers are commercially available from, for example, BD Biosciences (Pharmingen), San Diego, Calif.

Primary antibodies can be labeled with a fluorophore (i.e., fluoroscein isothiocyanate, phycoerythrin, Cy5, Cy5.5, Cy7-allophycocyanin (APC)), or can be bound by a labeled secondary antibody specific for the constant region of the primary antibodies (i.e., anti-mouse, anti-rat, anti-hamster, anti-rabbit, anti-goat, anti-sheep, anti-human, etc.). Primary or secondary antibodies can be purchased labeled with a fluorophore or can be purchased unlabeled and labeled as necessary for use in a particular assay. Fluorescent dyes of use in labeling primary or secondary antibodies for use in flow cytometry can be purchased, for example, from Molecular Probes, Eugene, Oreg. When simultaneously evaluating the presence or absence, or differential presence, of two or more immune cell markers, the labeled antibodies each should be conjugated to fluorescent labels with emission spectra detectably distinct from one another.

In a further aspect, the present invention provides methods for identifying one or more polypeptide markers indicative of a neurodevelopmental disorder, including an autism spectrum disorder, said method comprising:

(a) obtaining a mass spectrum of one or more polypeptides in a high molecular weight fraction from a test sample from an individual having a neurodevelopmental disorder, including an autism spectrum disorder; and (b) comparing the mass spectrum from said test sample to a corresponding high molecular weight fraction mass spectrum from a control sample from an individual not having a neurodevelopmental disorder, wherein said one or more polypeptide markers indicative of a neurodevelopmental disorder is identified by the presence or absence, or differential presence, of one or more proteins between said test sample and said control sample.

In a further aspect, the present invention provides methods for identifying one or more metabolite markers indicative of a neurodevelopmental disorder, including an autism spectrum disorder, said method comprising:

(a) obtaining a mass spectrum of one or more metabolite markers in a low molecular weight fraction from a test sample from an individual having a neurodevelopmental disorder, including an autism spectrum disorder; and (b) comparing the mass spectrum from said test sample to a corresponding low molecular weight fraction mass spectrum from a control sample from an individual not having a neurodevelopmental disorder, wherein said one or more metabolite markers indicative of a neurodevelopmental disorder are identified by the presence or absence, or differential presence, of one or more metabolites between said test sample and said control sample.

In obtaining a mass spectrum of components in a sample from an individual, mass spectrometry techniques well known in the art are applied. See, for example, Dass, *Principles and Practice of Biological Mass Spectrometry*, 2001, John Wiley; Niessen, *Liquid Chromatography: Mass Spectrometry*, 2003, Marcel Dekker; *Liquid Chromatography/Mass Spectrometry MS/MS and Time of Flight MS: Analysis of Emerging Contaminants*, Ferrer and Thurman, eds., 2003, American Chemical Society; Kinter and Sherman, *Protein Sequencing and Identification Using Tandem Mass Spectrometry*, 2000, John Wiley; and Byrdwell, *Modern Methods for Lipid Analysis by Liquid Chromatography/Mass Spectrometry and Related Techniques*, 2005, AOCS Press. The particular mass spectrometry approach applied will depend on several factors, including, for example, the size and kind (protein, lipid, carbohydrate, nucleic acid, small organic molecule) of the components in the spectrum, the volatility of the components, and the ultimate resolution required. For example, non-volatile components can be subject to liquid chromatography-electrospray ionization mass spectrometry (LC-ESI-MS). Instruments having time-of-flight (TOF or quadrupole TOF, Q-TOF) detection allow for high resolution separation and identification of different components. Components of particular interest can be subject to tandem mass spectrometry (MS/MS) for differential quantification and molecular identification. Laser desorption/ionization mass spectrometry also finds use in the present methods. Volatile components can be subject to gas chromatography-electron-impact ionization-mass spectrometry (GC-EI-MS).

Prior to analysis by mass spectrometry, components in a sample typically are fractionated into one or more fractions according to molecular weight. The categorization of a "high molecular weight" fraction, a "low molecular weight" fraction, and any "mid-molecular weight fractions," for the purposes of the present invention (obtaining a proteome or metabolome profile) can be defined at any molecular weight(s) appropriate to the assay being conducted, for instance, corresponding to molecular weight cut-off values of commercially available filters or dialysis membranes (Millipore, Billerica, Mass.; Pierce Biotechnology, Rockford, Ill.). Accordingly, a high molecular weight fraction can comprise components having a mass greater than about 3.5 kilodaltons (kDa), 5.0 kDa, 7.0 kDa, 10 kDa, 30 kDa, 60 kDa, or 100 kDa. Similarly, a low molecular weight fraction can comprise components having a mass less than about 3.5 kDa, 5.0 kDa, 7.0 kDa, 10 kDa, 30 kDa, 60 kDa, or 100 kDa. In one embodiment, the high molecular weight fraction components from a sample are those having a mass greater than about 5 kDa. In one embodiment, the low molecular weight fraction components from a sample are those having a mass less than about 5 kDa.

In certain embodiments, the components of a sample are separated prior to analysis by mass spectrometry according to one or more properties, for example, size, charge, hydrophobicity, hydrophilicity, kind of molecule (protein, lipid, carbohydrate, nucleic acid, small organic molecule). In one embodiment, polypeptide components are separated according to size and charge, for example, by sequential chromatographic steps (size exclusion and ionic exchange, including cationic or anionic exchange) or by 2-dimensional gel electrophoresis. In one embodiment, polypeptide components are separated by size alone, for example, using liquid chromatography or gel electrophoresis. Separation of polypeptide components can be accomplished using protein purification techniques well known in the art, described, for example, in Cutler, *Protein Purification Protocols*, $2^{nd}$ edition, 2004, Humana Press; and in Roe, *Protein Purification Applications: A Practical Approach*, $2^{nd}$ edition, 2001, Oxford University Press. Guidance for liquid chromatographic preparation of samples prior to analysis by mass spectrometry can be found, for example, in Ferrer and Thurman, eds.,2003, supra; Byrdwell, 2005, supra; Niessen, 1998, supra; *High Performance Liquid Chromatography: Fundamental Principles and Practice*, Lough, et al., eds., 1996, Luwer Academic Pub.; and *Protein Liquid Chromatography*, Kastner, ed., 1999, Elsevier Science Ltd.

In certain embodiments, the components of a sample are cleaved into smaller oligomers prior to analysis by mass spectrometry, for example, by exposure to one or more hydrolytic enzymes, including one or more proteases, nucleases, glycosidases, lipases, phospholipases, phosphatases, and sulfatases.

When preparing polypeptide components in a sample for mass spectrometry analysis, the most abundant proteins in the sample are usually removed to increase the dynamic range for evaluation of the remaining proteins. For example, the most abundant proteins in a blood, serum or plasma sample include albumin, IgG, IgA, haptoglobin, transferrin and antitrypsin. The remaining proteins are then usually exposed to one or more proteolytic enzymes, typically digestive enzymes, including trypsin, chymotrypsin, papain, pepsin, and carboxypeptidase A. The cleaved polypeptide segments then are typically separated according to one or more properties (i.e., size and/or charge), as described above.

A presence or absence, or differential presence, of one or more components in a sample (polypeptides, metabolites) is demonstrated by a differential mass spectrum, wherein the detection by mass spectrometry of certain components is increased or decreased in a sample from an individual with a neurodevelopmental disorder, including an ASD, in comparison to a sample without a neurodevelopmental disorder or with a different neurodevelopmental disorder. A presence or absence, or differential presence, can be determined by visual inspection of quantified signals of one or more components in a mass spectrum provided by a mass spectrometer. Typically, the quantified signals of one or more sample components are compared between two or more samples from individuals and a determination of a statistical difference between the samples is carried out. A presence or absence, or differential presence, also can be determined without statistical analysis. A differential presence (either increased or decreased) of one or more sample components is identified when one sample gives a quantifiable signal that is, for example, 10%, 20%, 30%, 40%, 50%, 75%, 1-fold, 2-fold, 3-fold, 4-fold different from the one or more other samples being tested (i.e., a control or a sample from an individual with a different neurodevelopmental disorder).

Generally, in practicing the methods of the present invention of identifying biomarkers indicative of a neurodevelopmental disorder, a sample from an individual is typically a fluid tissue sample, for example, blood, serum, plasma or cerebrospinal fluid.

Optionally, in practicing the methods of the present invention of identifying biomarkers indicative of a neurodevelopmental disorder, the presence or absence, or differential presence, of one or more immune cell markers, one or more polypeptide markers and/or one or more metabolite markers is statistically correlated with the presence of a neurodevelopmental disorder in an individual as compared to an individual who does not have a neurodevelopmental disorder (e.g., autism spectrum disorder versus a normal control), or in comparison to an individual who has a different neurodevelopmental disorder (e.g., high functioning autism versus low functioning autism).

The statistical test applied will depend on the number of groups being compared and the nature of the data. For example, when comparing two groups, normally distributed data can be analyzed using parametric statistical tests (i.e., a t-test), and unevenly distributed data can be analyzed using nonparametric statistical tests (i.e., a Wilcoxon or Kiruskal-Wallis rank test). Goodness-of-fit statistics (Shapiro-Wilk) and tests of skewness and kurtosis are performed to assess normality. The statistical evaluation of three or more groups can be done using analysis of variance (ANOVA) tests. Guidance for the application of statistics can be found, for example, in Devore, *Probability and Statistics for Engineering and the Sciences With Infotrac*, 2003, Thomson Learning; Gravetter and Wallnau, *Statistics for the Behavioral Sciences*, 2003, Thomson Learning; Samuels, et al., *Statistics for the Life Sciences*, 2002, Prentice Hall; and Tabachnick and Fidell, *Using Multivariate Statistics*, 2001, Allyn and Bacon.

Generally, in practicing the methods of the present invention of identifying biomarkers indicative of a neurodevelopmental disorder, samples are taken from an individual wherein the diagnosis of the presence or absence of a neurodevelopmental disorder has been previously determined by a physician according to currently applied neuropsychological evaluation standards.

Methods of Diagnosis

In one aspect, the present invention provides methods for diagnosing the susceptibility to a neurodevelopmental disorder, including an autism spectrum disorder, in an individual, said method comprising:

determining the presence or absence, or differential presence, of one or more markers indicative of a neurodevelopmental disorder, including an autism spectrum disorder, in a sample from a first individual suspected of having a susceptibility to a neurodevelopmental disorder, the one or more markers selected from the group consisting of one or more immune cell markers, and one or more polypeptide markers.

In one embodiment, the increased or decreased presence of said one or more markers are determined in comparison to a sample from a second individual who does not have a neurodevelopmental disorder or who has a different neurodevelopmental disorder.

In a further aspect, the present invention provides methods for diagnosing the susceptibility to a neurodevelopmental disorder, including an autism spectrum disorder, in an individual, said method comprising: determining the presence or absence, or differential presence, of one or more markers indicative of a neurodevelopmental disorder, including an autism spectrum disorder, in a sample from a first individual suspected of having a susceptibility to a neurodevelopmental disorder, the one or more markers selected from the group consisting of one or more immune cell markers, one or more polypeptide markers, and one or more metabolite markers.

In one embodiment, the increased or decreased presence of said one or more markers are determined in comparison to a sample from a second individual who does not have a neurodevelopmental disorder or who has a different neurodevelopmental disorder.

In carrying out the methods of diagnosis, the one or more markers indicative of a neurodevelopmental disorder were previously identified according to the methods described above, using cytometry to determine the presence or absence, or differential presence, of one or more immune cell markers, and mass spectrometry to determine the presence or absence, or differential presence, of one or more polypeptide or metabolite markers, optionally with statistical correlations of the presence or absence, or differential presence, of the one or more markers with a neurodevelopmental disorder.

In one embodiment, the one or more markers are polypeptide markers. The polypeptide markers can be full-length proteins or fragments of proteins (i.e., peptides). The peptides can be from a mature protein, or from a signal peptide and/or a propeptide of a protein.

However, the methods of diagnosis can be carried out using either cytometry or mass spectrometry or other methods of detection well known in the art, depending on the marker being identified for establishing a diagnosis. For example, if the diagnosis of a neurodevelopmental disorder, including an ASD, is based on the differential presence of one or more polypeptide markers (e.g., proteins or peptides), the presence or absence, or differential presence, conveniently can be detected using well known immunoassay methods. See, for example, *The Immunoassay Handbook*, Wild, ed., 2005, Elsevier Science Ltd.; Ghindilis, Pavlov and Atanassov, *Immunoassay Methods and Protocols*, 2003, Humana Press; Harlow and Lane, *Using Antibodies: A Laboratory Manual*, 1998, Cold Spring Harbor Laboratory Press; and *Immunoassay Automation: An Updated Guide to Systems*, Chan, ed., 1996, Academic Press. The particular method carried out for the purposes of diagnosing a neurodevelopmental disorder, including an ASD by identifying the presence or absence, or differential presence of the one or more biomarkers previously identified according to the methods described herein is not critical. In certain instances, for instance when a diagnosis can be determined based on the presence or absence of one or more established biomarkers, it is not necessary to compare to a control sample from an individual without a neurodevelopmental disorder or to a sample from an individual with a different neurodevelopmental disorder.

In one embodiment, the methods of the present invention provide for diagnosing the susceptibility to an autism spectrum disorder in an individual, said method comprising: determining the differential presence of one or more markers indicative of an autism spectrum disorder in a sample from a first individual suspected of having a susceptibility to an autism spectrum disorder, the one or more markers selected from the group consisting of one or more immune cell markers, one or more polypeptide markers, and one or more metabolite markers.

In a further embodiment, the increased or decreased presence of said one or more markers are determined in comparison to a sample from a second individual who does not have an autism spectrum disorder indicates that said first individual has a susceptibility to an autism spectrum disorder. The autism spectrum disorder can be high functioning autism or low functioning autism.

In one embodiment, the autism spectrum disorder is indicated by the differential presence of one or more immune cell markers selected from the group consisting of increased HLA-DR+ CD8+ T cells, increased CD26− CD8+ T cells, decreased CD26+ CD8+ T cells, increased CD38− CD8+ T cells, decreased CD32+ neutrophils, increased numbers of B cells, and increased numbers of natural killer (NK) cells.

In one embodiment, the autism spectrum disorder is indicated by the differential presence of one or more polypeptide markers selected from the group consisting of one or more polypeptides synthesized in the liver, one or more one polypeptides involved in a lipid metabolism pathway, one or more polypeptides involved in a coagulation pathway, one or more polypeptides involved in a complement pathway, one or more polypeptides involved in neuronal morphogenesis, and one or more polypeptides involved in synaptic transmission.

In one embodiment, the one or more polypeptides are involved in a complement pathway. In one embodiment, the autism spectrum disorder is indicated by the differential presence of one or more complement pathway polypeptide markers selected from the group consisting of increased complement factor H-related protein 1 (FHR-1), decreased complement component 3 (C3), increased complement C1q subcomponent C chain (C1q), increased fibronectin 1 (FN1), and decreased complement component 4B (C4b). In one embodiment, the autism spectrum disorder is indicated by the differential presence of a set of complement pathway polypeptide markers comprising increased complement factor H-related protein 1 (FHR-1), decreased complement component 3 (C3), increased complement C1q subcomponent C chain (C1q), increased fibronectin 1 (FN1), and decreased complement component 4B (C4b).

In one embodiment, the autism spectrum disorder is indicated by the increased presence of one or more polypeptide markers selected from the group consisting of serotransferrin, afamin, prothrombin (coagulation factor II), alpha-2-antiplasmin, antithrombin-III, apolipoprotein A-I, apolipoprotein A-II, apolipoprotein A-IV, apolipoprotein E, apolipoprotein M, hemopexin (beta-1B-glycoprotein), transferrin, inter-alpha-trypsin inhibitor heavy chain H2, inter-alpha-trypsin inhibitor heavy chain H1, kininogen, alpha 2 macroglobulin, complement factor H, inter-alpha (globulin) inhibitor, heparin cofactor II, inter-alpha-trypsin inhibitor heavy chain-related protein, alpha-2-HS-glycoprotein, vitronectin, fibrinogen beta chain, fibrinogen beta chain preprotein, complement component C9, fibronectin, group-specific component (vitamin D binding protein), fibronectin 1 isoform 1 preproprotein, keratin 1, clusterin isoform 1, angiotensinogen, angiotensin, coagulation factor X, Ig mu chain C region, insulin-like growth factor binding protein complex acid labile chain, complement factor H-related protein 1, serum amyloid A-4 protein precursor, kallistatin, corticosteroid-binding globulin, carboxypeptidase N 83 kDa chain, cytochrome P450 11A1, serum paraoxonase/arylesterase 1, protein kinases (EC 2.7.1.37) cdc2-related PSSALRE (SEQ ID NO:18) (of cdc2 family of kinases), mac-2-binding glycoprotein, potassium voltage-gated channel subfamily C member 1, selenoprotein P, DNA replication licensing factor MCM6, cullin homolog 7, serine (or cysteine) proteinase inhibitor, clade C, myosin binding protein C, X-prolyl aminopeptidase 2, tumor necrosis factor (TNF)-alpha converting enzyme, eukaryotic translation initiation factor 2-alpha kinase 3, ecotropic viral integration site 5, peptidoglycan recognition protein L, and Histone regulation (HIR) (histone cell cycle regulation defective, *S. cerevisiae*) homolog A.

In one embodiment, the autism spectrum disorder is indicated by the decreased presence of one or more polypeptide markers selected from the group consisting of apolipoprotein B-100, ferroxidase (EC 1.16.3.1), inter-alpha-trypsin inhibitor heavy chain H4, alpha-1-antichymotrypsin, complement factor B preproprotein, plasma kallikrein, alpha-1-acid glycoprotein 1, alpha-1-acid glycoprotein 2, histidine-rich glycoprotein, transthyretin, fibrinogen alpha/alpha-E chain, hemopexin, cell surface glycoprotein CD11b, aspartate aminotransferase, vitamin K-dependent protein S, WNT3 protein (a human homologue of *Drosophila* wingless), cytokeratin 9, complement component C8 alpha chain, clathrin heavy chain 1, desmoplakin 1, extracellular matrix protein 1, extracellular matrix protein 1 precursor (secretory component p85), dihydropyrimidinase related protein-2, serine (or cysteine) proteinase inhibitor, clade A, brain-specific angiogenesis inhibitor 2, centromere protein F (350/400 kD), ADP-ribosylation factor (ARF), GTPase-activating protein GIT2 (G protein-coupled receptor kinase-interactor 2), paraoxonase 1, carnosinase 1, phosphofructokinase, hypothetical protein FLJ20967, abnormal spindle (asp)-like protein, and dedicator of cytokinesis protein 1 (DOCK 180).

In one embodiment, the autism spectrum disorder is indicated by the differential presence of one or more polypeptide markers selected from the group consisting of decreased apolipoprotein B, increased transferrin, increased TNF-alpha converting enzyme (TACE), decreased dedicator of cytokinesis protein 1 (DOCK 180) and increased complement factor H-related protein (FHR-1).

In one embodiment, the autism spectrum disorder is indicated by the differential presence of one or more polypeptide markers selected from the group consisting of increased TNF-alpha converting enzyme (TACE), increased breast cancer antigen BRCA1, increased complement factor H-related protein 1 (FHR-1), decreased complement component 3 (C3), decreased apolipoprotein B-100, increased complement C I q subcomponent C chain (C1q), increased fibronectin 1 (FN1), and decreased complement component 4B (C4b). In one embodiment, the autism spectrum disorder is indicated by the differential presence of a set of polypeptide markers comprising increased TNF-alpha converting enzyme (TACE), increased breast cancer antigen BRCA1, increased complement factor H-related protein 1 (FHR-1), decreased complement component 3 (C3), decreased apolipoprotein B-100, increased complement C1q subcomponent C chain (C1q), increased fibronectin 1 (FN1), and decreased complement component 4B (C4b).

In one embodiment, the autism spectrum disorder is indicated by the differential presence of one or more metabolite markers are selected from the group consisting of a polypeptide, a carbohydrate, a lipid, a nucleic acid and a small organic compound.

In one embodiment, the autism spectrum disorder is indicated by the differential presence of one or more metabolite markers are selected from the group consisting of a hormone, a vitamin, a neurotransmitter, and a phospholipid. In one embodiment, the autism spectrum disorder is indicated by the differential presence of a phosphocholine.

In a further aspect, the present invention provides methods for distinguishing high functioning autism from low functioning autism, the method comprising: determining the comparative or differential presence of one or more markers indicative of an autism spectrum disorder in a sample from an individual suspected of having an autism spectrum disorder, the one or more markers selected from the group consisting of one or more immune cell markers, one or more polypeptide markers, and one or more metabolite markers to control samples containing one or more markers known to be indicative of high functioning autism or low functioning autism.

In one embodiment, low functioning autism is indicated by an increased presence of one or more polypeptide markers selected from the group consisting of mitotic arrest deficient-like-1 (MAD-like-1), apolipoprotein B-100, apolipoprotein A-IV, cytomatrix protein p110, apolipoprotein C-II, Wnt-9a, Wnt-14, WD repeat domain 17, complement C1r component, complement component C9, complement component C8 beta chain, clusterin isoform 1, complement-associated protein AP-40, complement factor I (C3B/C4B inactivator), fibronectin, and nuclear receptor coactivator 4 (NCoA-4). In one embodiment, low functioning autism is indicated by an increased presence of one or more polypeptide markers selected from the group consisting of mitotic arrest deficient-like-1 (MAD-like-1), apolipoprotein B-100, apolipoprotein A-IV, cytomatrix protein p 110, apolipoprotein C-II, Wnt-9a, Wnt-14, and WD repeat domain 17.

The increased presence can be measured relative to a sample or known value from a normal individual or relative to a sample or known value from an individual with high functioning autism. The sample from the individual suspected of having low functioning autism can be compared to control samples from normal individuals, from individuals with high functioning autism or from individuals having low functioning autism.

Generally, in practicing the methods of the present invention of diagnosing a neurodevelopmental disorder, a sample from an individual is typically a fluid tissue sample, for example, blood, serum, plasma or cerebrospinal fluid.

Generally, in practicing the methods of the present invention of diagnosing a neurodevelopmental disorder, the differential presence of one or more immune cell markers, one or more polypeptide markers and/or one or more metabolite markers was previously statistically correlated according to the methods described herein with the presence of a neurodevelopmental disorder in an individual as compared to an individual who does not have a neurodevelopmental disorder (e.g., autism spectrum disorder versus a normal control), or in comparison to an individual who has a different neurodevelopmental disorder (e.g., high functioning autism versus low functioning autism).

In one embodiment, the methods of diagnosis include further correlating the differential presence of one or more immune cell markers, one or more polypeptide markers and/or one or more metabolite markers with the presence of one or more autoimmune diseases in the individual's relatives (i.e., a familial history of autoimmune disease). The autoimmune disease can be T-cell mediated (e.g., autoimmune uveitis, multiple sclerosis) or humorally mediated (e.g., rheumatoid arthritis, myasthenia gravis, systemic lupus erythematosus).

Kits

In a further aspect, the present invention provides kits for diagnosing the susceptibility to a neurodevelopmental disorder, including an autism spectrum disorder, in an individual, said kit comprising:

a set of reagents for determining the presence or absence, or differential presence, of one or more markers indicative of a neurodevelopmental disorder, including an autism spectrum disorder, in a sample from an individual suspected of having a susceptibility to a neurodevelopmental disorder, the one or more markers selected from the group consisting of one or more immune cell markers, one or more polypeptide markers and/or one or more metabolite markers.

In one embodiment, the kit contains a set of antibodies for detecting one or more immune cell markers, one or more polypeptide markers and/or one or more metabolite markers indicative of a neurodevelopmental disorder, including an autism spectrum disorder.

In one embodiment, the kit contains one or more antibodies for detecting the presence or absence or differential presence of HLA-DR, CD8, CD26, CD32, CD38, B cells (e.g., CD19, CD20, CD45, CD5, CD27, CD38, CD40, CD44, CD62L, CD69, CD71, CD80, CD86, CD95, HLA-DP, HLA-DQ, HLA-DR, and PAN), and natural killer (NK) cells (e.g., CD56, NKB1, CD2, CD7, CD8, CD57 and CD94) in a sample comprising immune cells.

In one embodiment, the kit contains antibodies for detecting the presence or absence or differential presence of one or more polypeptide markers in a complement pathway. In one embodiment, the kit contains antibodies for detecting one or more polypeptide markers selected from the group consisting of TNF-alpha converting enzyme (TACE), breast cancer antigen BRCA1, complement factor H-related protein 1 (FHR-1), complement component 3 (C3), apolipoprotein B-100, complement C1q subcomponent C chain (C1q), fibronectin 1 (FN1), and complement component 4B (C4b). In one embodiment, the kit contains antibodies for detecting a set of polypeptide markers comprising TNF-alpha converting enzyme (TACE), breast cancer antigen BRCA1, complement factor H-related protein 1 (FHR-1), complement component 3 (C3), apolipoprotein B-100, complement C1q subcomponent C chain (C1q), fibronectin 1 (FN1), and complement component 4B (C4b).

EXAMPLES

The following examples are offered to illustrate, but not to limit the claimed invention.

Example 1

The present example presents a cross-sectional study that demonstrates statistically significant differences in biomarkers (i.e., cell-surface proteins, polypeptides in blood, serum or plasma) between two cohorts: children with an autism spectrum disorder (70 subjects) and healthy, normal controls (35 subjects). The children with an autism spectrum disorder were further subdivided into high functioning (HFA, 35 subjects) and low functioning (LHA n=35) autism groups based on an intelligence quotient (IQ).

The study employed a comprehensive phenotyping platform (Kantor A B, *Dis Markers*, 18:91(2002); Kantor A B et al., *Clin Immunol*, 111:186(2004)) to identify biomarkers. Samples were provided for evaluation of 1) cellular markers using microvolume laser scanning cytometry with the SuroScan™ system (SurroMed, LLC, Menlo Park, Calif.) for multi-parameter cellular analysis and 2) proteomic and metabolomic markers using liquid chromatography-mass spectrometry analysis. The cellular assays tracked over 1000 primary and secondary variables, including cell counts, cell ratios and cell surface antigen intensities. The LC-MS data were analyzed with SurroMed's MassView™ software (SurroMed, LLC, Menlo Park, Calif.) to yield relative quantitative information for over 6000 molecular species with a median coefficient of variance of about 25% for the proteome components and 40% for the LC-metabolome components.

There were multiple differences in cell populations between the Autism and Normal groups. Significant differences among the cell counts of B cells and natural killer (NK) cells were observed. The absolute number of B cells per volume of blood was about 20% higher for children with autism with a p-value of 0.003. Similarly the absolute number of NK cells was about 40% higher for children with autism with a p-value of 0.01. Neither of the variables shows significant difference between the low and high functioning autism groups.

There were multiple differences in the proteome between the Autism and Normal groups. A very high fraction (65%) of the components with p-values less than 0.05 were identified by linkage to a peptide library and additional directed tandem mass spectrometry. Groups of proteins related to synaptic transmission, neuronal morphogenesis and coagulation that were different between the two cohorts.

Methods

Study Design

A total of 136 children between 4 to 6 years of age were enrolled in the investigation. Participants were recruited from the University of California at Davis M.I.N.D. Institute Clinic and research database. Typically, developing participants were recruited from area school districts and community centers.

The inclusion criteria for the autism group included a diagnosis of Autistic Disorder based on the DSM-IV criteria determined by an experienced neuropsychologist (B.A.C.), which was further corroborated by the following measures. *The Autism Diagnostic Observation Schedule-Generic* (ADOS-G) (Lord, et al., *J Autism Dev Disord* (2000) 30:205; and Lord, et al., Autism Diagnostic Observation Schedule (ADOS), Western Psychological Services, Los Angeles, Calif.) provides observation of a child's communication, reciprocal social interaction, and stereotyped behavior including an algorithm with cut-offs for autism and autism spectrum disorders. *The Autism Diagnostic Interview-Research* is a comprehensive, semi-structured parent interview that assesses a child's developmental history and relevant behaviors characteristic of autism and generates a diagnostic algorithm for Autistic Disorder (Lord, *J Autism Dev Disord* (1994) 24:659). Children who did not meet full autism criteria including pervasive developmental disorder-not otherwise specified (PDD-NOS) and Asperger Syndrome were excluded from the study. *The Social Communication Questionnaire* (SCQ) (Berument, *Br J Psychiatry* (1999) 175:444) was used as a screening tool to ensure the absence of symptoms of autism in the typically developing control children. Children who had scores above the cutoff (score=15) were excluded from the typically developing group, and were referred for further diagnostic evaluation.

*The Stanford-Binet Intelligence Scale* (Thorndike, et al., *The Stanford Binet Intelligence Scale*, Fourth edition, Riverside Publishing Co., Itasca, Ill.), is a standardized measure of cognitive functioning administered to all participants to provide a measure of overall intellectual ability (IQ). The broad average range is defined by a mean of 100 and a standard deviation of 16. The autism group was further divided based on IQ as follows: High functioning autism (HFA) having an IQ>68 and low-functioning autism (LFA) having an IQ<68. Inclusion criteria for typically developing children (TYP) were: evidence of attaining normal developmental milestones; no diagnosis of autism or other developmental disabilities; and IQ>68.

A comprehensive medical history form, the *AGRE Medical History Forms* (AGRE), was given to the parents of all participants to provide demographic, medical and family history information. For the purpose of this evaluation, we report only findings pertaining to familial immune disorders. Subjects were excluded from the investigation if they had a diagnosis of Fragile X or other serious neurological (e.g., seizures), psychiatric (e.g., bipolar disorder) or known medical conditions. All participants were screened via parental interview for current and past physical illness. Children with known endocrine, cardiovascular, pulmonary, liver or kidney disease were excluded from enrollment in the study. Furthermore, failure to complete significant portions of the research protocol resulted in exclusion from the study. Twenty-two children were excluded due to failure to meet inclusion criteria or noncompliance with the protocol. Further, the blood sample of one child with LFA was later determined unusable.

The final study group consisted of 104 children, 69 children with autism matched for age and gender with 35 children in the typical developing group. Of the children with autism, 35 had HFA and 35 (34) LFA. The gender ratio was the same across all three groups with 29 males and 6 females in each group. The HFA group had a mean age of 5.2 years and mean IQ of 79. The LFA group had a mean age of 5.5 years and a mean IQ of 56. The Typical group had a mean age of 5.7 years and an average IQ of 115. Participation in the study required two visits. During the first visit the ADIR, ADOS, Stanford Binet and parental interviews were performed that lasted approximately 3 ½ hours. The second visit consisted of a blood draw by a professional, pediatric phlebotomist at the M.I.N.D. Institute.

The following describes a cross-sectional phenotyping study between children with Autism (Group A) and healthy controls (Group N, Normal). The children with Autism were further subdivided into high functioning (HFA) and low functioning (LHA) groups based on IQ. Demographics for the 104 subjects used in the analysis are presented in Table 1. Groups were well matched for gender and age.

TABLE 1

Study Subjects

| Characteristic | HFA | LFA | N |
|---|---|---|---|
| N | 35 | 35 (34) | 35 |
| Male % | 83 | 83 | 83 |
| Age (Med) | 5.2 | 5.5 | 5.7 |
| IQ | 79 | 56 | 115 |
| Caucasian % | 63 | 60 | 86 |
| Hispanic % | 14 | 17 | 0 |

Sample Collection Procedures

Parents were asked to have their child fast prior to the blood draw, which required no consumption of food after midnight the evening before the collection. The serum sample was collected in one 9.5 mL serum separator tube. Immediately following collection, the tube was inverted five times to mix clot activator with the blood. The blood was allowed to clot for 30 minutes at room temperature in a vertical position. The tube was centrifuged at room temperature within one hour of collection for 10 minutes at 1200 RCF (2400 rpm, Eppendorf 5810 centrifuge with an A-4-62 rotor). The samples were then sent chilled to SurroMed Corporation (San Jose, Calif.). SurroMed personnel were blind to the diagnosis until after all samples were assayed. The University of California at Davis Internal Review Board (IRB) approved this study.

Analytical Methods

Cellular Assays

The protocol included 64 three-color cellular assays performed by microvolume laser scanning cytometry (MLSC) on SurroScan™ system (SurroMed, LLC) (Dietz L J et al., *Cytometry*, 23:177 (1996); Kantor A B et al., *Biotechniques* 36:520 (2004); Walton I D et al., *Microvolume laser scanning cytometry platform for biological marker discovery*, Presented at Proc. SPIE-Int.Soc. Opt. Eng. (2000)). The assays are well suited for evaluating immune and inflammatory processes. Monoclonal antigen-specific antibodies were purchased from various commercial vendors and developed into assays. Three different fluorophores, Cy5, Cy5.5 (Mujumdar R B et al., *Bioconjug Chem*, 4:105 (1993); Southwick P L et al., *Cytometry*, 11:418 (1990)) and the tandem dye Cy7-APC (Beavis A J and Pennline K J., *Cytometry*, 24:390 (1996); Roederer M et al., *Cytometry*, 24:191 (1996)), were coupled to individual monoclonal antibodies specific for different cellular antigens in each assay. Each fluorophore was measured in a separate detection channel. The antibody-dye reagents were combined into pre-made cocktails and all assays were homogeneous, without removal of unreacted antibody reagents. Aliquots of whole or red blood cell-lysed blood were added to 96 well micro-titer plates containing the appropriate reagent cocktails, incubated in the dark at room temperature for 20 minutes, diluted with an appropriate buffer and loaded into Flex32™ capillary arrays (SurroMed, LLC) and analyzed with SurroScan™ (SurroMed, LLC). Images were converted to a list-mode data format with software (Norton S M et al., *Proc. SPIE-Int. Soc. Opt. Eng.*, 3921:20 (2000)). Fluorescence intensities were compensated for spectral overlap of the dyes so values are proportional to antigen density.

Quality and baseline measures were developed and established with twenty blood bank samples for the 64 different three-reagent cellular assays used in this study. Standard template gates are established using these results plus additional staining controls for all individual reagents and two-color combinations. Template gates are established using FlowJo™ cytometry analysis software (Tree Star, Inc., Ashland, Oreg.) customized for SurroMed to enable upload of gates to an Oracle database. Gating information is stored in the database and applied to the scan data for each assay using SurroGate™ database-driven cytometry analysis software (SurroMed, LLC) in order to generate the resulting cell count and antigen intensity data.

The assay panel allows the enumeration of major cell populations: granulocytes, eosinophils, monocytes, CD4+ and CD8+ T cells, B cells, and NK cells. It allows finer phenotyping of cell types based on the expression of the activation antigens, co-stimulatory molecules, adhesion molecules, antigen receptors, cytokine receptors, etc. The assays monitor cell counts of more than 200 different cell populations, plus the relative levels of the different cell surface antigens on specific populations.

Cytometry Data Collection. Template gates were used to enumerate the cell populations of interest in all of the assays. Invalid assays and those that do not support the template gates are flagged. An analyst visually reviewed all assay results prior to data upload. In this study 105 subject samples were analyzed with 64 assays for a total 6720 assays.

An additional 18 samples were received early in the study and processed for cytometry. These are not included in the statistical analysis because the Normal subjects did not match up well with the Autism group in terms of gender and age.

Among the assays 0.67% were invalid due to technical difficulties and are excluded from the analysis. An additional 4.8% required non-standard gates. These results are used in the statistical analysis. Cell counts are generally not affected, but cell surface expression results may have a larger variation.

Mass Spectrometry

The serum samples were subjected to mass spectrometric analysis for differential expression of proteins and metabolites, and identification of components in the fluid. For each sample, the material was analyzed for low molecular weight (LMW) and high molecular weight (HMW) components. First the biological fluid was separated based on molecular weight range (LMW=below about 5 kDa and HMW=above abour 5 kDa). A schematic of the processing is shown in FIG. 1. Software was used to track and quantify molecules for their differential expression.

Proteome

The proteomic, high-molecular-weight (HMW) fraction has the six most abundant proteins (albumin, IgG, IgA, haptoglobin, transferrin and antitrypsin) substantially depleted by an affinity resin to increase the effective dynamic range of the measurements. The remaining proteins were denatured, disulfide bonds reduced, and sulfhydryl groups carboxymethylated prior to digestion by modified trypsin. During this process, low molecular weight molecules were excluded during a buffer exchange step with a 5-kDa cut-off filter.

The tryptic peptides were then profiled (individual molecules tracked across samples and their differential presence quantified) by liquid chromatography-electrospray ionization-mass spectrometry (LC-ESI-MS) on high-resolution (R>5,000) time-of-flight (TOF) instruments using a capillary chromatography column. The on-line chromatography used was reverse-phase chromatography for one-dimensional (1-D) chromatography with a water/acetonitrile 100-minute gradient, and 0.1% formic acid added to aid in ionization efficiency and chromatographic behavior. Software was used to track and quantify molecules for their differential expression.

Identification of proteins occurs via identification of peptides. Peptides of interest (significantly changing in expression level) are linked to tandem mass spectrometry (MS/MS) experiments on quadrupole-time-of-flight (Q-TOF) and ion-trap mass spectrometers using extra or similar sample material. The resulting MS/MS spectra contain fragmentation patterns with characteristic peptide backbone cleavages. Each MS/MS raw spectrum from an isolated precursor ion is compared using commercially available software with in silico protein digestion and fragmentation using NCBI's RefSeq database to find a match, and hence identification. A match-quality score is reported. This identification approach also applies to peptides found in the LC-MS low-molecular-weight fraction. In some instances, de novo sequencing is also employed (no database matching) using one of several commercial software packages.

Metabolome

The metabolomic, low-molecular-weight (LMW) fraction was obtained from approximately one hundred microliters of the plasma by first removing proteins by precipitation with the addition of an organic solution. The supernatant containing the LMW fraction was transferred from the solution by pipetting. This LMW material was further divided into two fractions.

One fraction was for the volatile or volatilizable small molecule components analyzed by gas chromatography-electron-impact ionization-mass spectrometry (GC-EI-MS). Volatilization was enhanced by trimethylsilyl derivatization of active hydrogens. The carrier gas was helium.

The second fraction was for analysis of nonvolatile components by liquid chromatography-electrospray ionization-mass spectrometry (LC-ESI-MS) using reverse phase (RP) chromatography. In this LC-MS analysis, low molecular weight free-floating peptides were detected in addition to metabolites. This LC-ESI-MS arrangement, with reverse-phase capillary HPLC, was similar to that used for the tryptic peptides from the proteomic fraction. For LC-MS, high-resolution (R>5,000) time-of-flight mass spectrometers were used for profiling, while for GC-MS, a quadrupole mass spectrometer was used with unit mass resolution although accurate mass by TOF-MS is available for GC-MS on select samples to aid with identifications.

For molecular identification of the volatile low molecular weight molecules, electron-impact ionization provides characteristic fingerprint fragmentation patterns that can lead to identification if the molecule has been analyzed previously in pure form and entered into a database, including the one provided by National Institute of Standards and Technology (NIST) and the Kyoto Encyclopedia of Genes and Genomes (KEGG). Otherwise, use of accurate mass to constrain the elemental composition is also useful, and finally, tandem mass spectrometry (MS/MS) is available with a triple-quadrupole instrument. For those molecules tracked and deemed to be of interest due to their significant differential expression, even if an initial attempt at identification was not successful (no molecular name given in the results) one can later obtain identification with further effort, sometimes requiring isolation from the complex mixture.

For identification of the LMW fraction studied by LC-MS, a primary tool in the case of peptides is MS/MS (described above, for the case of digested proteins). Of importance especially for metabolites is accurate mass determination (usually to within a few mDa) to constrain elemental composition, and use of data sources such as the *Dictionary of Natural Products, Merck Index*, and the NIST and KEGG databases to infer identity. Comparison of mass spectrum and chromatographic retention time with pure compound, if available, can provide a definitive identification. MS/MS is a primary tool for metabolites as well as polypeptides because it can be used to corroborate identity or provide insight into an unknown's structure. A molecule of interest also can be purified and subjected to NMR analysis. A schematic of the standard identification logic is shown in FIG. 2.

Quantification strategy. We applied an approach to quantification of LC-MS data, applicable to large numbers of proteins/peptides and metabolites for the purpose of differential expression measurements and discovery of biomarkers that has been described (Becker C H, Mass spectrometric quantification of chemical mixture components, U.S. Pat. No. 6,835,927 (2002); Wang W, et al., *Anal Chem*, 75:4818 (2003)). In this situation, many or most monitored proteins are unanticipated at the time of laboratory study, thus eliminating the possibility of prior investigation of relative sensitivity factors (RSFs). Furthermore, methods based on introducing a known amount of a chemically analogous extraneous substance as an internal standard (i.e. "spiking" of a standard reference material) are not practical, whether the analog is chemically identical and isotopically labeled (the isotope dilution method) or based on chemical similarity.

The differential quantification method used here relies on the changes in analyte signal intensities directly reflecting their concentrations in one sample relative to another. Samples are not mixed nor are the samples otherwise manipulated beyond that required for the LC-MS analysis itself. The sample preparation and LC-MS conditions need to be carefully controlled, however, for optimal results, and frequent quality control samples are analyzed to assure stable, reproducible performance. Generally, similar samples are compared in the method, such as blood, serum, plasma or cerebrospinal fluid from different human subjects.

This quantification technology employs overall spectral intensity normalization by employing signals of molecules that do not change concentration from sample to sample. In this way, a simple correction can be applied for any drift over time in overall LC-MS instrument response and/or differences in sample concentrations. We used MassView™ software (SurroMed, LLC), which among other functions, performs normalization by determining the median of the ratios for a large number of molecular components, requiring no operator intervention. The MassView™ software also performs the following automated functions: spectral smoothing, baseline subtraction, noise evaluation, isotopic analysis, peak identification, intensity evaluation, inter-scan evaluation to construct chromatographic peaks, inter-file (inter-sample) evaluation to establish molecular components for analysis, normalization (mentioned above), and finally, quantification for the thousands of components. When spectra are sparse and simple, spectral analysis similarly is simple. In the present case, the great complexity of the LC-MS spectra with associated identification, tracking and quantification of many thousands of molecular components is likewise more analytically challenging.

Quantification for GC-MS is done by referencing the intensity of all molecular components to one or two isotopically labeled and spiked components in the complex mixture. The simpler chromatography and ionization, relative to LC-MS, makes this a feasible approach for quantification. Peak identification is performed via the Automated Mass Spectral Deconvolution and Identification System (AMDIS) program published by National Institutes of Standards and Technology (available on the worldwide web at chemdata.nist.gov/mass-spc/amdis/). This program deconvolutes electron-impact ionization mass spectra over chromatographic time and components are tracked using a library. Each entry in the library representing a distinct molecular component is constrained by a tight chromatographic elution time window and mass fingerprint pattern.

Mass Spectrometry Data Collection. Among the three analyses, less than 1% of the samples were invalid due to technical difficulties. These were excluded from the statistical analyses. For the LC Proteome, data for one subject (MIA104) is invalid due to due to missing Cysteine protection peaks in the profile data. For the LC Metabolome data for one subject (MIA064) in invalid due to poor LC MS data related to sample preparation.

Statistical Methods

Cytometry. Statistical analyses were conducted to assess differences in cell populations, proteomic variables and metabolomic variables 1) between combined autistic groups (HFA+LFA) and control group (N); 2) between each of the subgroup combinations and 3) among the three groups. Comparisons for cytometry are listed in Table 2.

TABLE 2

Statistical Comparisons - Cytometry

| Type | Groups |
|---|---|
| 2 Group | A (LHA + HFA) vs. N |
| | LFA vs. N |
| | HFA vs. N |
| | LFA vs. HFA |
| 3 Group | LFA, HFA, N |

With regard to two-group statistics, we apply to all data a univariate mean comparison test that will be either parametric or non-parametric depending on the normality of the data. If the data are approximately normally distributed, the parametric statistics will be used (t-test); if not, the nonparametric rank test (Wilcoxon or Kiruskal-Wallis test) will be applied. All tests of hypotheses will be two-sided. Goodness-of-fit statistics (Shapiro-Wilk) and tests of skewness and kurtosis are performed to assess normality. The evaluation of the three-group comparison is done by ANOVA.

The data set for this study is broad, i.e., there are many more variables than subjects. Consequently, many multivariate statistics such as multivariate analysis of variance, which require more subjects than variables, could not be conducted. Instead, a more conservative approach had to be used to analyze the data: Univariate tests were performed on individual variables, and the step-down Bonferroni p-value adjustment method of Holm (Blair RC et al., Control of familywise errors in multiple endpoint assessments via stepwise permutation tests, 15:1107 (1996); Holm S., *In Scand J Stat*, pp. 65 (1979)) was employed to control for multiple comparisons. This maintained the overall type-I error rate (false positives) at 0.05 for the different hypothesis tests conducted; however, the univariate p-values must be increasingly smaller to remain significant after adjustment as the number of comparisons grows. One advantage of the step-down Bonferroni method is that a combination of parametric and non-parametric p-values can be used.

Cytometry variables. Our hypothesis tests included 644 variables from cell counts and cell surface antigen intensities. Multiple measures of the same cell population (e.g., CD4+ T cells) were combined into a single average for the analysis. Variables for this reduced variable list are designated as S1 in the cytometry result tables. Overall results are reported for 1273 S1 and S2 variables. The S2 variables are informative, but may be redundant with S1 variables. The conservative step-down Bonferroni adjustment method gives us confidence in the validity of the significant adjusted results for this high number of comparisons. These results are discussed and presented with the appropriate adjusted p-value. Additionally, trends based on results at multiple univariate levels are also discussed (univariate p-value). This study was underpowered for the number of variables being studied, and some informative results could be overlooked if the univariate statistics were ignored. In this study with 644 S1 variables, differences at the univariate p-value of 0.01 or lower, warranted further consideration.

Mass spectrometry. Comparisons for the mass spectrometry data sets are listed in Table 3. The sample matching and sample run order enable the use of paired tests to generate the primary statistics for these data sets. For these comparisons, results are ranked by univariate p-value.

TABLE 3

Statistical Comparisons - Mass Spectrometry

| Type | Groups |
|---|---|
| 2 group, unpaired | A (LHA + HFA) vs. N |
| 2 group, paired | A (LHA + HFA) vs. N |
| 2 group, paired | LFA vs. N |
| 2 group, paired | HFA vs. N |
| 2 group, paired | LFA vs. HFA |

Results

Cytometry

Summary Statistics

A summary of the significant measures for each of the comparisons is shown in Table 4 for the cytometry results. For each statistical level (p-value) the number of false-positive variables expected to appear by chance (assuming all are independent) is given in the first column. Detailed lists of the all of the variables are provided in the electronic Result Tables, which are described under Supporting Material.

The number of observed significant differences depends on the effect size (difference between the means/standard deviation) and the number of samples measured. There were multiple significant differences observed in the comparison of the autistic children and the controls (A vs N). In general, more and greater differences are observed between children with Autism and Normal than between the two LFA and HFA subgroups and control or each other.

TABLE 4

Significant Measures for Study comparisons - Counts and Intensity*

| Parameter | Chance | Autism vs Normal | HFA vs Normal | LFA vs Normal | HFA vs LFA | HFA vs LFA vs Normal |
|---|---|---|---|---|---|---|
| Sample size | | 70, 35 | 35, 35 | 35, 35 | 35, 35 | 35, 35, 35 |
| Adjusted p ≦ 0.05 | <1 | 1 | 0 | 4 | 0 | 1 |
| p ≦ 0.001 | <1 | 21 | 3 | 22 | 1 | 12 |
| p ≦ 0.01 | 6 | 77 | 25 | 76 | 7 | 54 |
| p ≦ 0.05 | 32 | 151 | 101 | 162 | 33 | 139 |

*Based on 644 S1 variables. Variable counts at each p-value are cumulative

It is useful to separate the significant variables into counts and intensity measures. Table 5 and Table 6 show the significant measures for counts and intensities respectively.

TABLE 5

Significant Measures for Study comparisons - Counts only

| Parameter | Chance | Autism vs Normal | HFA vs Normal | LFA vs Normal | HFA vs LFA | HFA vs LFA vs Normal |
|---|---|---|---|---|---|---|
| Sample size | | 70, 35 | 35, 35 | 35, 35 | 35, 35 | 35, 35, 35 |
| Adjusted p ≦ 0.05 | <1 | 0 | 0 | 0 | 0 | 0 |
| p ≦ 0.001 | <1 | 5 | 1 | 2 | 0 | 2 |
| p ≦ 0.01 | 2 | 23 | 11 | 14 | 2 | 10 |
| p ≦ 0.05 | 11 | 43 | 42 | 39 | 4 | 36 |

* Based on 224 S1 count variables. Variable counts at each p-value are cumulative

TABLE 6

Significant Measures for Study comparisons - Intensity only

| Parameter | Chance | Autism vs Normal | HFA vs Normal | LFA vs Normal | HFA vs LFA | HFA vs LFA vs Normal |
|---|---|---|---|---|---|---|
| Sample size | | 70, 35 | 35, 35 | 35, 35 | 35, 35 | 35, 35, 35 |
| Adjusted p ≦ 0.05 | <1 | 1 | 0 | 4 | 0 | 1 |
| p ≦ 0.001 | <1 | 16 | 2 | 20 | 1 | 10 |
| p ≦ 0.01 | 4 | 54 | 14 | 62 | 5 | 44 |
| p ≦ 0.05 | 21 | 108 | 59 | 123 | 29 | 103 |

* Based on 420 S1 intensity variables. Variable counts at each p-value are cumulative Evaluation of Bias in Sample Collection This study had a higher proportion of autistic subjects at the beginning than at the end. We evaluated the results for systematic effects on the observed differences. This is particularly important for intensity variables, which need to be considered with some caution. Systematic differences can arise from drift in the instrument or individual reagents. Standard beads are run with every sample and can be used to monitor systematic instrument errors. Very small differences between bead intensities were measured with the autistic group and beads measured with the control group. The largest difference, about 3%, was observed for the Cy7APC beads. This small difference had a univariate p-value of <0.05. About 20% of the intensity variables (20 out of 108) at the p<0.05 level have differences greater than 15% in the Autism vs. Normal comparison and are worth further consideration.

Intensity Variables

Subjects in the different cohorts are not distributed evenly over time. A higher proportion of the normal subjects were collected at the end of the study. There is a small decrease in intensity of anti-CD4 (Cy7-APC reagent) on CD4 T cells over the time course of the study. The samples into two sets where there was a natural pause in the collection of samples. Set 1 contains 71% of the Autistic Group, but only 34% of the controls (Table 7).

TABLE 7

Subjects in Set 1 and 2

| | SUBJECT | | |
|---|---|---|---|
| | HFA | LFA | N |
| ALL | 35 | 35 | 35 |
| SET 1 | 24 | 26 | 12 |
| SET 2 | 11 | 9 | 23 |

The mean CD4 relative cell intensity (RCI), is 6.3% higher in the autistic group vs. controls, with a p-value of 0.0005. However, when set 1 and set 2 are considered individually the difference is only 2.8 and 2.3% respectively and the p-values were not significant. Moreover, with cohort ratios of set 1 to set 2, there were differences of about 10%. Thus we do not attach biological meaning to the small differences in CD4 intensity between the autistic and control cohorts.

We reviewed the 20 intensity variables with differences between the cohorts of >15% and univariate p-values<0.05. The variables are listed in Table 8. Some of these are based on very low cell counts and were not pursued. Others are affected by the sample collection time bias. Results for HLA-DR on CD8+ T cells and CD32 on a neutrophil subset are discussed in the context of potential time bias.

TABLE 8

Intensity Difference in Mean for AUTISM vs. NORMAL >15% (S1 Variables)

| Var Id | Population | Intensity | Trend | AUTISM (N = 70) | | NORMAL (N = 35) | | P-Value | | % Ratio |
|---|---|---|---|---|---|---|---|---|---|---|
| | | | | Mean | SD | Mean | SD | USED | AdjP | |
| Intensity Differences > 31% | | | | | | | | | | |
| 4946 | CD16pCD66bpCD52n | CD52 | ↑ | 4453.5 | 1399.0 | 3395.8 | 1622.2 | 0.0003 | 0.16 | 131 |
| 5416 | CD4pnCD14pCD95p | CD95 | ↑ | 3632.8 | 1629.4 | 2764.9 | 705.8 | 0.002 | 1.00 | 131 |
| 5482 | CD3pCD4nHLADRp | HLA-DR | ↑ | 2746.0 | 2019.5 | 2073.8 | 1281.9 | 0.02 | 1.00 | 132 |
| 4623 | CD4pnCD14pCD25p | CD4 | ↑ | 254.2 | 189.5 | 193.6 | 196.0 | 0.04 | 1.00 | 131 |
| Intensity Differences 25-30% | | | | | | | | | | |
| 4651 | CD7pCD8pCD26p | CD26 | ↑ | 1149.0 | 390.5 | 887.4 | 202.4 | 0.0001 | 0.07 | 129 |
| 4388 | Neutrophil-CD66b Ch1 Ave | CD66b | ↑ | 4574.8 | 1275.6 | 3531.8 | 1310.6 | 0.0001 | 0.07 | 130 |
| 4949 | CD16pCD66bpCD52p | CD66b | ↑ | 4415.0 | 1392.3 | 3489.0 | 1284.5 | 0.002 | 0.96 | 127 |
| 5374 | CD8pnCD57pCD94p | CD94 | ↑ | 1911.4 | 1016.2 | 1473.3 | 780.4 | 0.04 | 1.00 | 130 |
| Intensity Differences 21-25% | | | | | | | | | | |
| 4449 | CCR5nCD8pCD60n | CD8 | ↑ | 2278.5 | 479.4 | 1873.8 | 451.7 | 0.0001 | 0.06 | 122 |
| 4800 | CD8pCD20nCD38n | CD8 | ↑ | 2762.6 | 691.0 | 2285.8 | 612.5 | 0.0008 | 0.52 | 121 |
| 5491 | CD3pCD4pHLADRp | HLA-DR | ↑ | 1166.5 | 626.2 | 964.7 | 991.0 | 0.0009 | 0.53 | 121 |
| 4495 | CD8nCD16p | CD101 | ↓ | 970.5 | 439.5 | 1228.0 | 383.2 | 0.0036 | 1.00 | 79 |
| 4738 | CD11bpnCD16pn | CD32 | ↓ | 745.7 | 573.1 | 964.1 | 685.6 | 0.03 | 1.00 | 77 |
| 4434 | CCR5pCD4pCD60p | CD4 | ↑ | 1594.7 | 920.9 | 1282.4 | 638.7 | 0.03 | 1.00 | 124 |
| Intensity Differences 16-20% | | | | | | | | | | |
| 5079 | CD8pCD45RApCD60p | CD8 | ↑ | 2717.3 | 462.1 | 2343.4 | 463.6 | 0.0004 | 0.26 | 116 |
| 5394 | CD8pCD20nCD95n | CD8 | ↑ | 2306.0 | 472.5 | 1981.9 | 404.1 | 0.0008 | 0.48 | 116 |
| 4736 | CD11bpCD16p | CD11b | ↑ | 2865.7 | 661.6 | 2390.0 | 691.0 | 0.0008 | 0.52 | 120 |
| 5321 | CD14nCD15pCD89p | CD15 | ↑ | 2478.2 | 619.4 | 2112.4 | 722.0 | 0.006 | 1.00 | 117 |
| 4825 | CD16pnCD18p | CD44 | ↓ | 1654.1 | 740.3 | 2004.0 | 808.5 | 0.0121 | 1.00 | 83 |
| 4456 | CCR5pCD8pCD60n | CCR5 | ↑ | 856.6 | 324.1 | 739.8 | 232.6 | 0.03 | 1.00 | 116 |

Figure 3A:
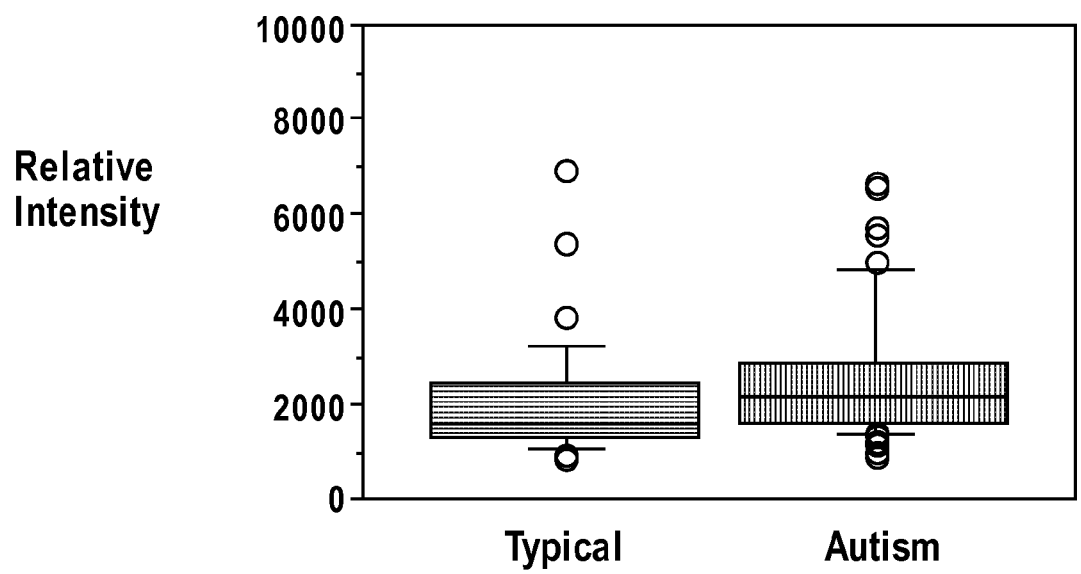
FIG. 3A. HLA-DR on CD8 T Cells. HLA-DR is 30% higher on CD8+ T cells in children with Autism vs. Normal. In this assay, CD8+ T cells were identified as CD3 positive, CD4 negative cells. The figure shows a comparison of relative intensity for Autistic (both high functioning and low functioning combined) vs. Normal subjects.
Figure 3B:
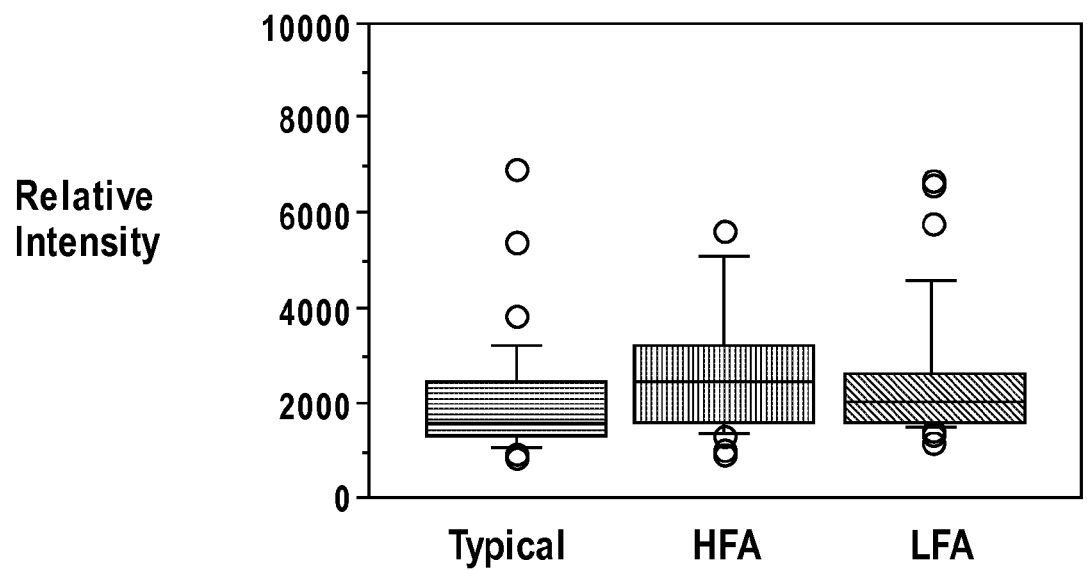
FIG. 3B. HLA-DR on CD8 T Cells. HLA-DR is higher on CD8+ T cells in children with Autism vs. Normal. In this assay, CD8+ T cells were identified as CD3 positive, CD4 negative cells. The figure shows a comparison of relative intensity for High Functioning Autistic and Low Functioning Autistic vs. Normal subjects.

HLA-DR is about 30-60% higher on CD8+ T cells in the Autism group than the Normal group (FIGS. 3A and 3B). This difference holds over the course of the study. It is observed at both the beginning (Set 1) and end (Set 2). The difference is greater for the HFA group than the LFA group.

Figure 3C:
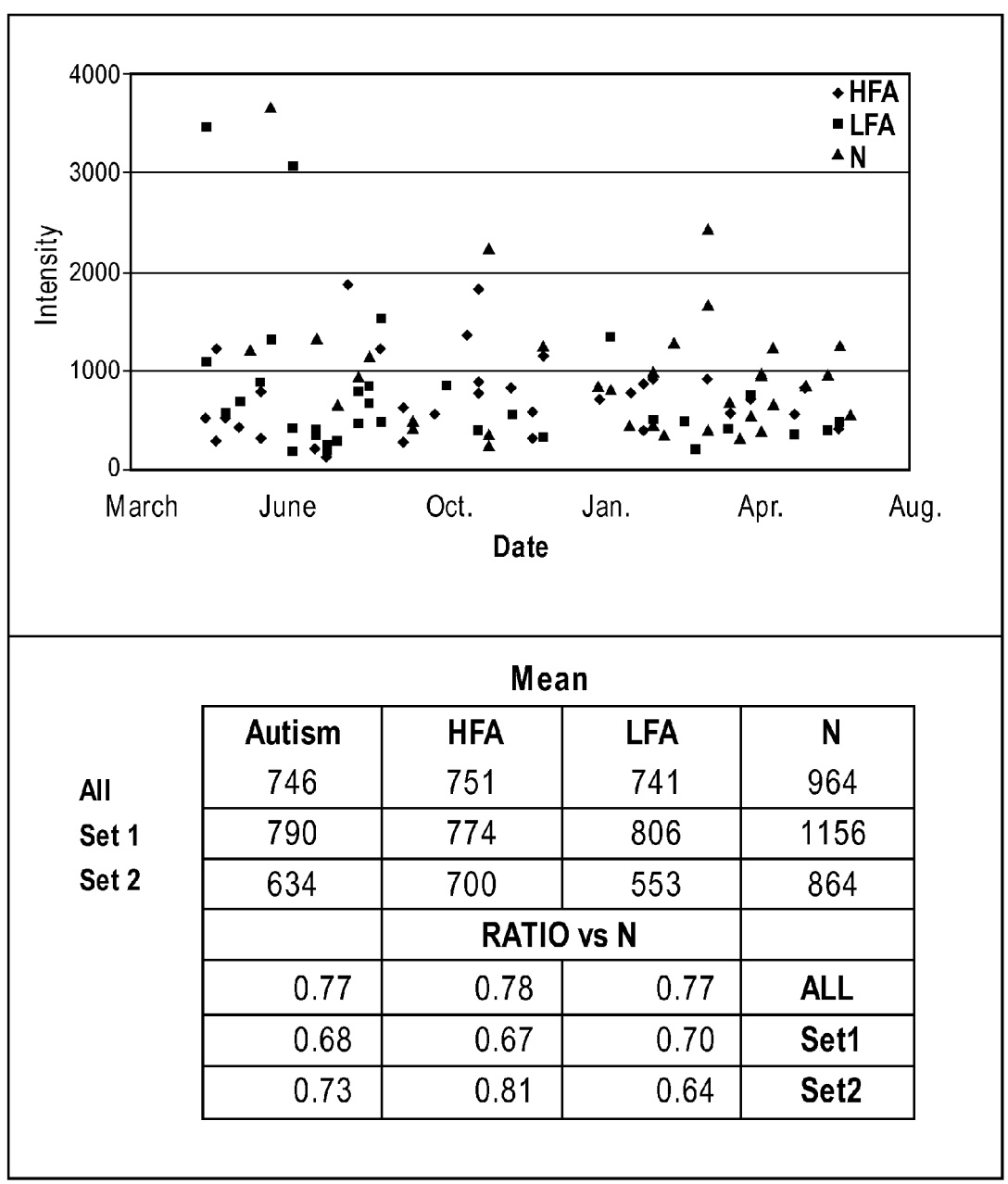
FIG. 3C. CD32 on Neutrophil subset. CD32 is lower on a neutrophil subset in children with Autism vs. Normal. Cell population is CD16 dim and CD11b dim. Top. Shows the intensity for subjects in all groups over time. Bottom. Means and ratios for All samples and Set 1 (early) and Set 2 (late) as defined in Table 7. Var 4738 N vs. A p-value=0.033. Set 1 v Set 2 comparisons are not significantly different.

CD32 is about 30% lower on a neutrophil subset in children with Autism vs. Normal (FIG. 3C). The cell population is CD16 dim and CD11b dim. This difference holds over the course of the study. It is observed at both the beginning (Set 1) and end (Set 2). The difference is the same for the HFA group and the LFA groups.

Cell Count Variables

Some select differences in cell populations and antigen densities between autistic and control groups are briefly noted in this section. Tables are grouped by category of cell populations. When appropriate, results are broken out by autism subgroups.

Most major cell populations are the same between the children with autism and controls. T cells, CD4+ T cells, CD8+ T cells, Neutrophils, total white blood cells (WBC), eosinophils and monocytes are not significantly different between the two groups (Table 9 and FIG. 4).

Figure 5:
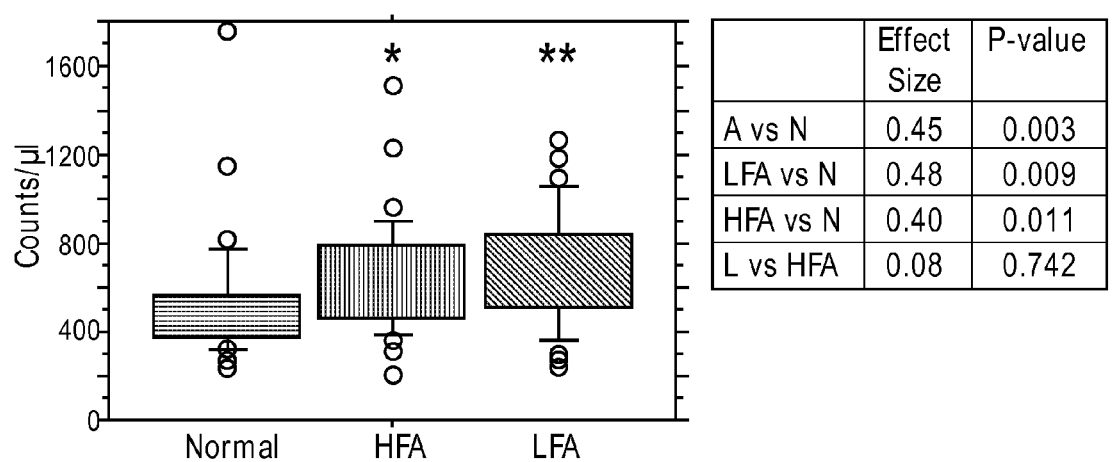
FIG. 5. B cells are higher in the autistic groups. Average B cell counts are higher in the HFA and LFA groups compared to controls. The average is based on 9 separate B cell assays that use the CD20 as the B cell identifier. P-values=* HFA vs N=0.011, ** LFA vs N=0.009, and A vs N 0.003. HFA vs LFA=not significant (0.7). The effect size (mean difference/standard deviation) is modest.

B cells. B cells are 20 to 25% higher in the Autism group compared with the Normal group. FIG. 5 shows the distributions for the Normal and Autism subgroups. The measure is an average based on nine separate B cell assays that use CD20 as the B cell identifier. The difference is significant at the univariate level for both HFA vs. controls, LFA vs controls and shows a trend of Normal<HFA<LFA, although there is no significant difference between the HFA and LFA groups.

TABLE 9

Comparison of major cell populations between Autism and Normal groups.

| Var ID | Cell Population | Trend | Normal N = 35* Mean | SD | Autism N = 70* Mean | SD | P-Values Uni | Adj |
|---|---|---|---|---|---|---|---|---|
| 3503 | T cells | — | 1834 | 629 | 1961 | 612 | 0.33 | 1 |
| 3483 | CD4 T cells | — | 1118 | 437 | 1211 | 459 | 0.33 | 1 |
| 3485 | CD4 T cells/T cells | — | 60.6% | 0.1 | 61.1% | 0.1 | 0.76 | 1 |
| 3487 | CD8 T cells | — | 664 | 267 | 686 | 249 | 0.56 | 1 |
| 3488 | CD8 T cells/T cells | — | 36.3% | 0.1 | 35.1% | 0.1 | 0.84 | 1 |
| 3481 | B cells | ↑ | 542 | 279 | 661 | 255 | 0.003 | 1 |
| 3482 | B Cells/WBC | ↑ | 7.3% | 2.9 | 8.2% | 3.0 | 0.062 | 1 |
| 3496 | Monocytes | — | 446 | 182 | 453 | 188 | 1.000 | 1 |
| 3498 | NK cells | ↑ | 117 | 80 | 161 | 95 | 0.011 | 1 |
| 3499 | NK cells/WBC | ↑ | 1.6% | 0.01 | 1.9% | 0.01 | 0.037 | 1 |
| 3505 | WBC | — | 7524 | 1783 | 8220 | 2238 | 0.169 | 1 |
| 3494 | Granulocytes | — | 3441 | 1474 | 3582 | 1519 | 0.557 | 1 |
| 3490 | Eosinophils | — | 286 | 225 | 438 | 515 | 0.066 | 1 |
| 3500 | Neutrophils | — | 3398 | 1490 | 3401 | 1435 | 0.747 | 1 |
| 3502 | Platelets | — | 1430357 | 505854 | 1613025 | 628482 | 0.188 | 1 |

*N is the number of subjects.

Total leukocytes (WBC), monocytes, and CD4+ and CD8+ T cells were not difference between the two groups. Differences were observed for B cells, which were higher by about 20% in autistic children and NK cells which were higher by almost 40% in autistic children (Table 9).

Table 10 includes data on some of the B cell subsetsa. In general differences in absolute cell counts for B cell subsets track with total B cells. For example, the absolute number of both CD5 positive and CD5 negative B cells are higher in the autistic children.

TABLE 10

Comparison of B cell subsets

| Var ID | Cell Population | Trend | Normal N = 35* Mean | SD | Autism N = 70* Mean | SD | P-Values Uni | Adj |
|---|---|---|---|---|---|---|---|---|
| 1 | B cells | ↑ | 542 | 279 | 661 | 255 | 0.003 | 1 |
| 2 | B Cells/WBC | ↑ | 7.3% | 2.9 | 8.2% | 3.0 | 0.062 | 1 |
| 93 | CD38n | ↑ | 164.49 | 99.32 | 193.40 | 84.59 | 0.013 | 1 |
| 94 | CD38p | ↑ | 394.65 | 199.91 | 479.71 | 210.22 | 0.0081 | 1 |
| 465 | CD38n/B cells | — | 0.29 | 0.07 | 0.29 | 0.10 | 0.98 | 1 |
| 467 | CD38p/B cells | — | 0.71 | 0.07 | 0.71 | 0.10 | 0.98 | 1 |
| 110 | CD5n | ↑ | 268.26 | 167.45 | 348.89 | 139.00 | 0.0001 | 1 |
| 111 | CD5p | ↑ | 278.32 | 142.06 | 329.39 | 171.76 | 0.14 | 1 |
| 616 | CD5n/B cells | — | 0.49 | 0.12 | 0.52 | 0.12 | 0.31 | 1 |
| 619 | CD5p/B cells | — | 0.51 | 0.11 | 0.48 | 0.12 | 0.31 | 1 |

Figure 4:
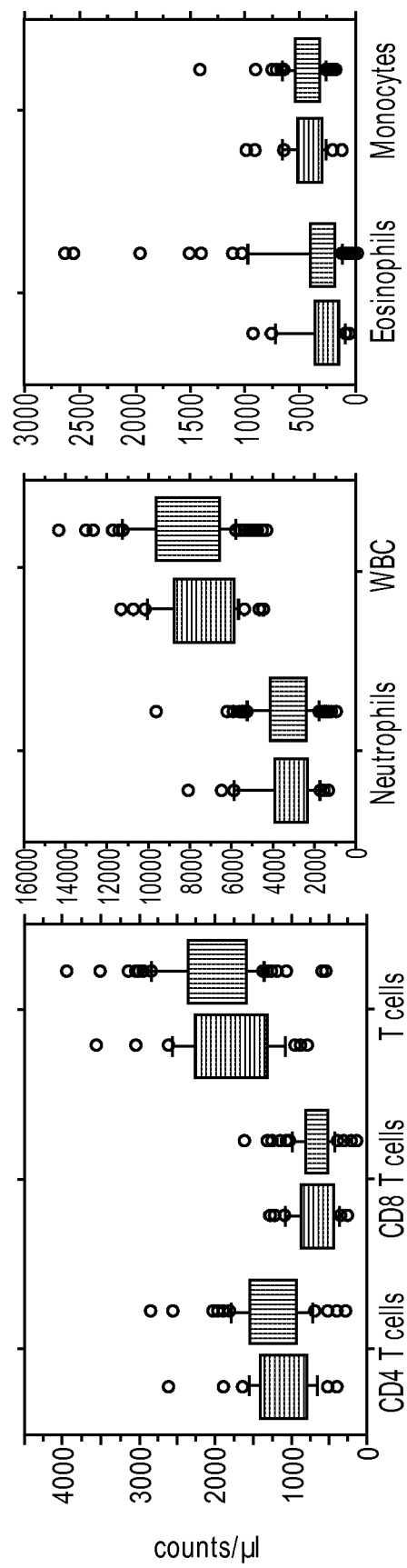
FIG. 4. Most major cell populations are the same between cohorts. All box and whisker plots in this report show: Median=Centerline, $25^{th}$ and $75^{th}$ percentile=bottom and top of box, $10^{th}$ and $90^{th}$ percentile=bottom and top whiskers, and individual points for the remaining events. Autism (vertical lines); Normal (horizontal lines).

Distributions of the major cell populations by cohort are shown in FIGS. 4-8. FIG. 4 shows box and whisker plots for Total T cells, CD4 T cells, CD8 T cells, neutrophils, total leukocytes (WBC) Eosinophils and monocytes. All of which are similar between the Autism and Normal groups.

B cell counts were evaluated for bias caused by time of collection. Significant differences in the fraction of B cells from the beginning and end of the study are not observed. In general, bias by time of collection is not observed for the major cell population count variables.

Figure 6:
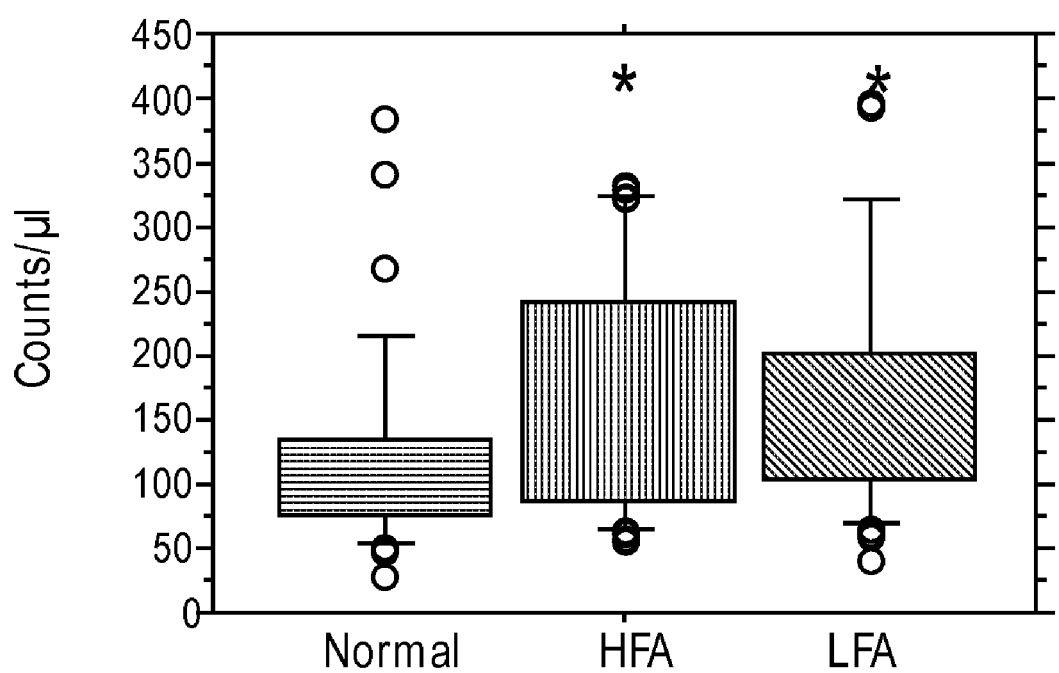
FIG. 6. NK cells are higher in the autistic groups. Average NK cell counts are higher in the HFA and LFA groups compared to controls. The average is based on 2 separate NK cell assays that use the CD56p and CD3n as the NK cell identifier. P-values=*HFA vs N=0.037, *LFA vs N=0.023, and A vs N=0.011. HFA vs LFA=not significant (0.8). Var 3498.

NK Cells. NK cells are about 40% higher in the autistic groups compared with controls. FIG. 6 shows the distributions. The measure is an average based on two separate NK cell assays that use CD56p and CD3n as the NK cell identifier. The difference is significant at the univariate level for both HFA vs. controls and LFA vs controls. There is no significant difference between the HFA and LFA groups. Table 11 shows that the same trend holds for the of higher NK cells in the autistic group holds for the individual assays.

NK cell counts were evaluated for bias caused by time of collection. NK cells did not show significant differences from the beginning to end of the study.

isotopes. The median CV's are about 31 and 32% for the Autism and Normal cohorts, which compare well with other human plasma studies.

Summary Statistics

A summary of the significant measures for each of the comparisons is shown in Table 13. The proteomic analysis tracked 6348 components. The most differences were observed in the Autism vs Normal comparison, which includes more samples (70 vs 35) than the other three comparisons (35 v 35). The number of hits that might be expected by chance, if all of the variables are independent, is also given

TABLE 11

Comparison of NK Cells

| Var ID | Cell Population | Trend | Normal N = 35* Mean | SD | Autism N = 70* Mean | SD | P-Values Uni | Adj |
|---|---|---|---|---|---|---|---|---|
| 3498 | NK cells | ↑ | 117 | 80 | 161 | 95 | 0.011 | 1 |
| 3499 | NK cells/WBC | ↑ | 1.6% | 0.01 | 1.9% | 0.01 | 0.037 | 1 |
| 3948 | CD2pCD3nCD56p | ↑ | 127 | 83.66 | 178.81 | 101 | 0.0046 | 1 |
| 3960 | CD3nCD56p (CD94t) | ↑ | 106 | 78.41 | 143.46 | 95 | 0.044 | 1 |

Figure 7A:
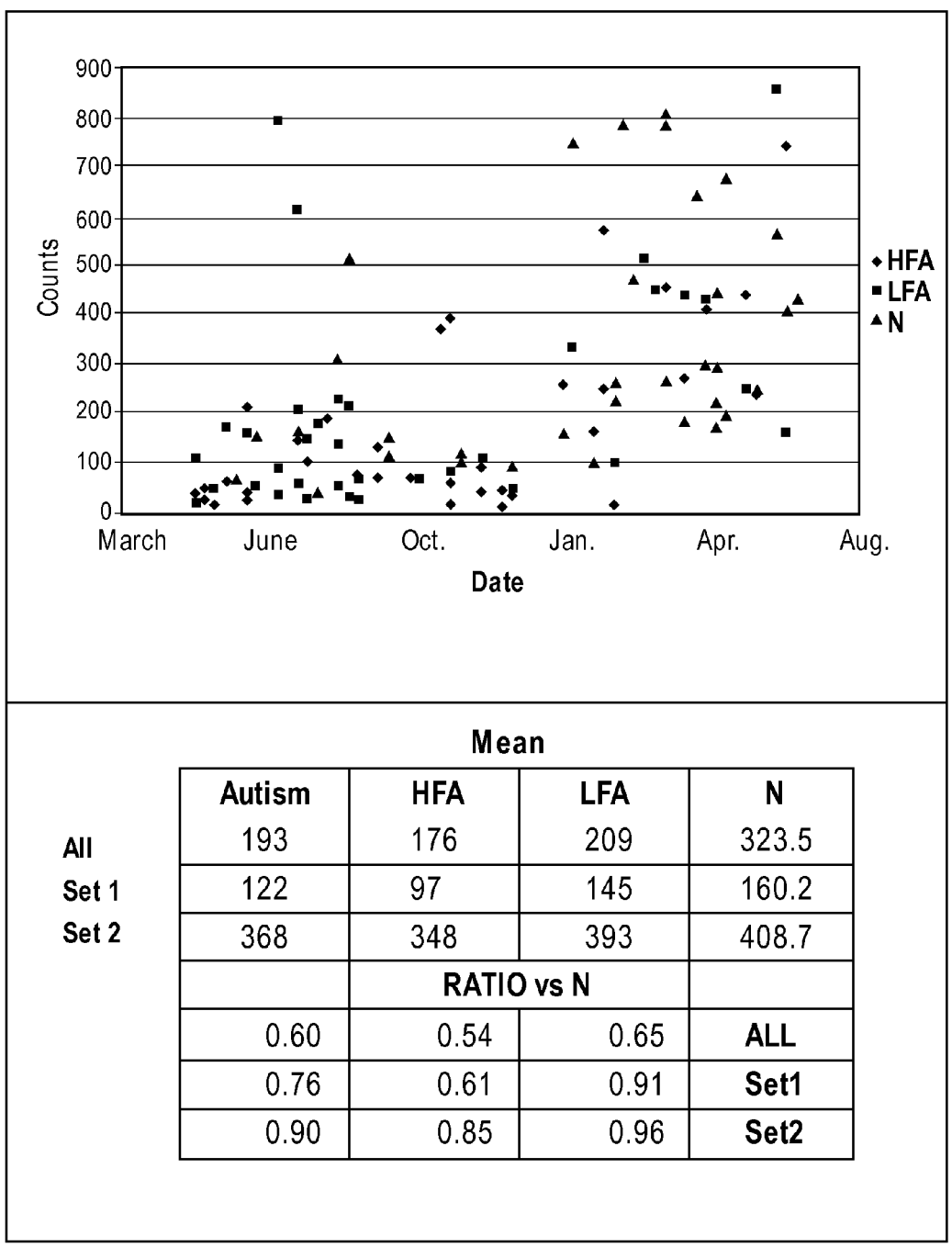
FIG. 7A. CD26+ CD8 T Cell counts. This subset of CD8 T cells shows a bias over time. Top. Shows the counts for subjects in all groups over time. Bottom. Means and ratios for all samples, Set 1 (early) and Set 2 (late) as defined in Table 7. A vs N p=0.0005. Set 1 v Set 2 comparisons for A and C, not significant. Var 3692
Figure 7B:
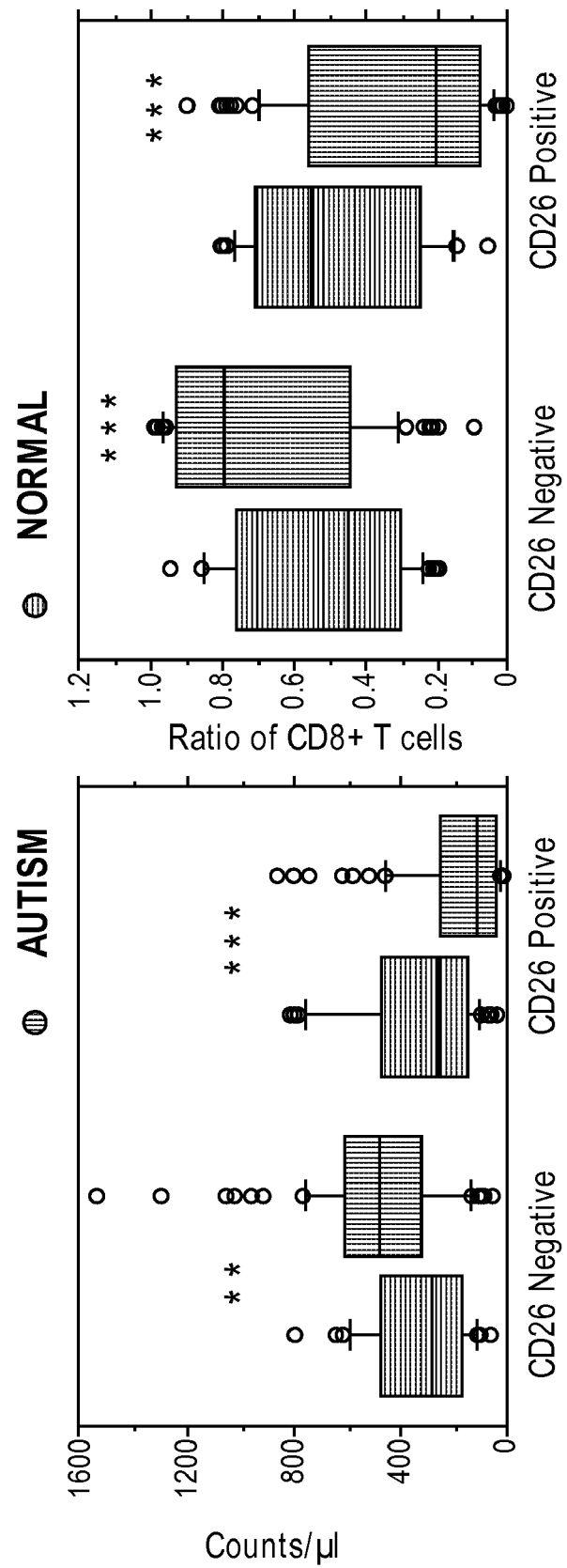
FIG. 7B shows box and whisker plots demonstrating that CD26 positive CD8+ T cells are lower in both absolute counts and relative counts to total CD8+ T cells. Further, CD26 negative CD8+ T cells are higher in both absolute counts and relative counts to total CD8+ T cells. Autism (red); Normal (blue).
Figure 8A:
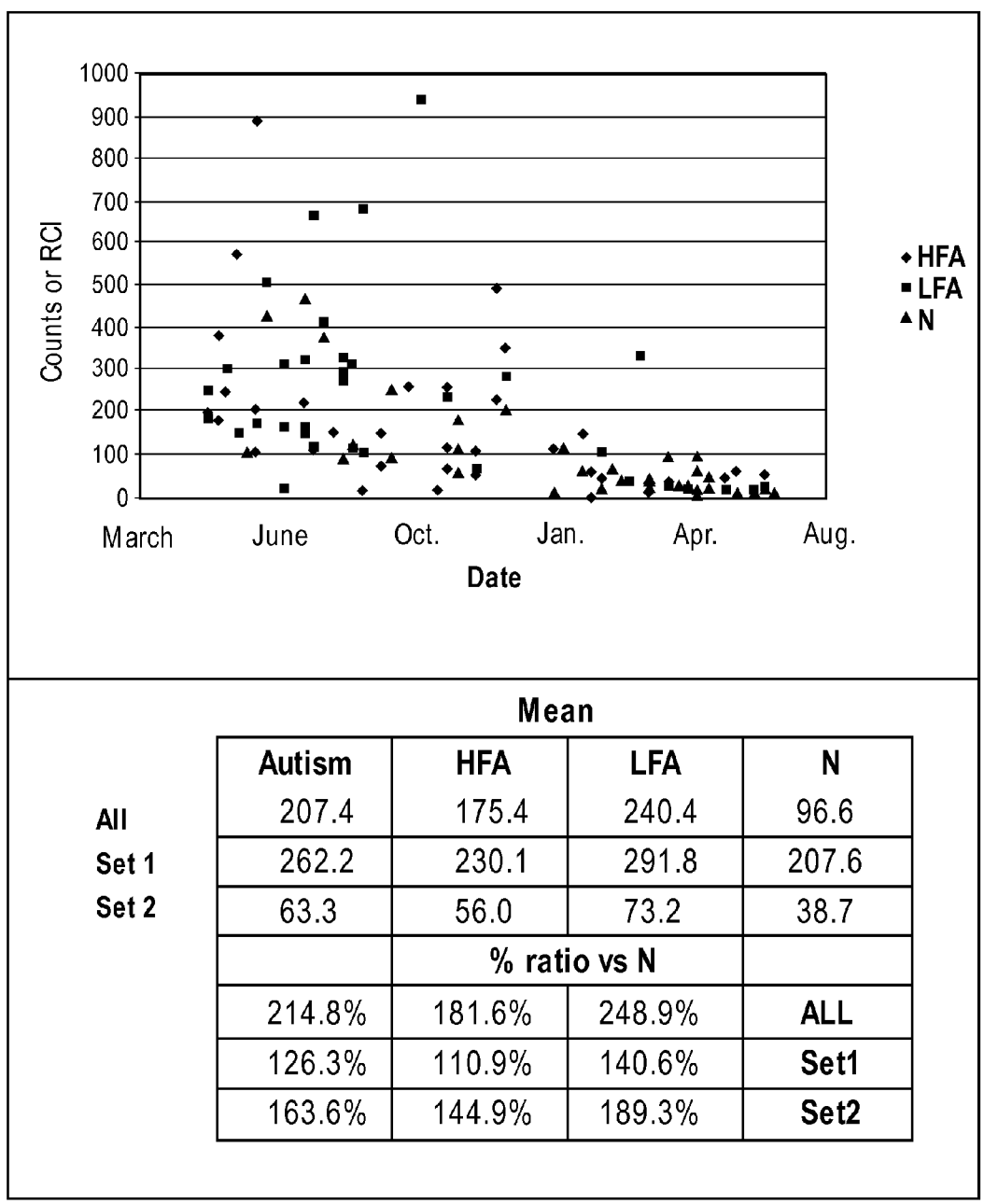
FIG. 8A. CD38 negative CD8 T Cell counts. This subset of CD8 T cells shows a bias over time. Top. Shows the counts for subjects in all groups over time. Bottom. Means and ratios for all samples, Set 1 (early) and Set 2 (late) as defined in Table 7. Set 1 vs Set 2, A: p=0.0001, N: p=4e-6. Var 3802
Figure 8B:
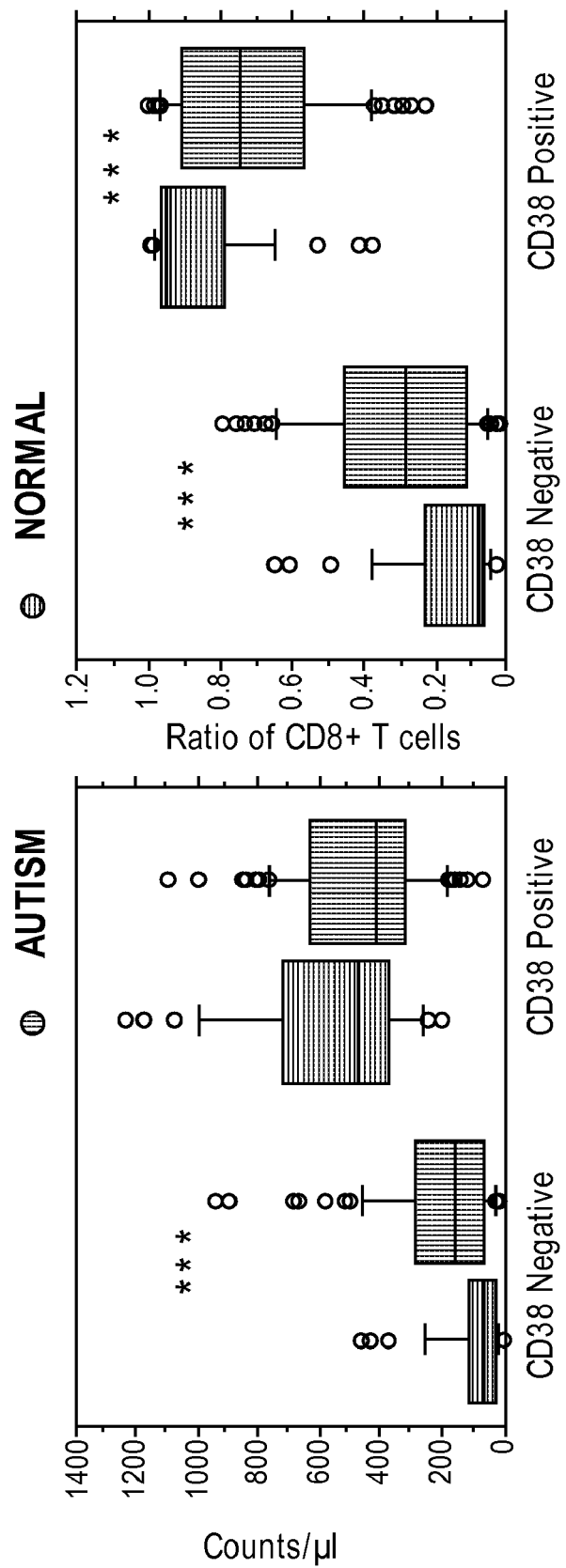
FIG. 8B shows box and whisker plots demonstrating that CD38 negative CD8+ T cells are higher in both absolute counts and relative counts to total CD8+ T cells. Autism (red); Normal (blue).

CD8+ T cell subsets. Several subsets of CD8+ T cells appear to be different between the Autism and Normal groups. Differences based on the CD26, a peptidase, which serves as a T cell co-stimulatory molecule and CD38, a marker of immune activation, are indicated in Table 12. Plots of the CD26+ and CD38+ CD8+T cell counts are shown in FIGS. 7 and 8. Significant differences in the fraction of positive cells for both markers from the beginning and the end of the study are observed. Determination of these smaller cell sub population is more dependent on assay drift than the major cell populations. Note that the CD26+ CD8 cells are lower in the Autism group for both time sets (FIG. 7B). Similarly, CD38+ CD8 cells are lower in the Autism group for both time sets (FIG. 8B).

in the table. In our experience, however, comparison of control vs. control yields half or less than what would be expected by chance at each p-value level.

Figure 9:
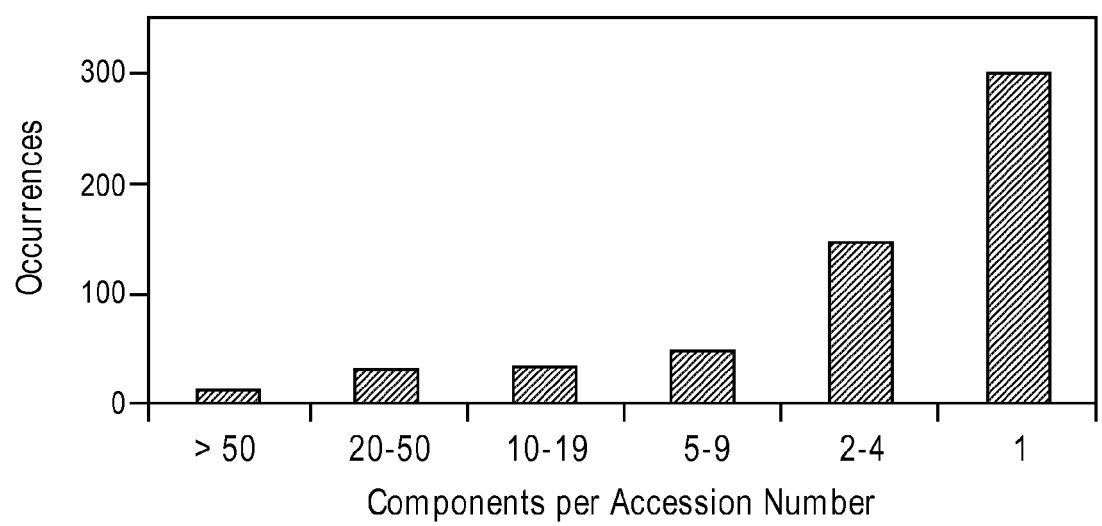
FIG. 9. Identification by Accession number. Components were identified with 576 different accession numbers.
Figure 10:
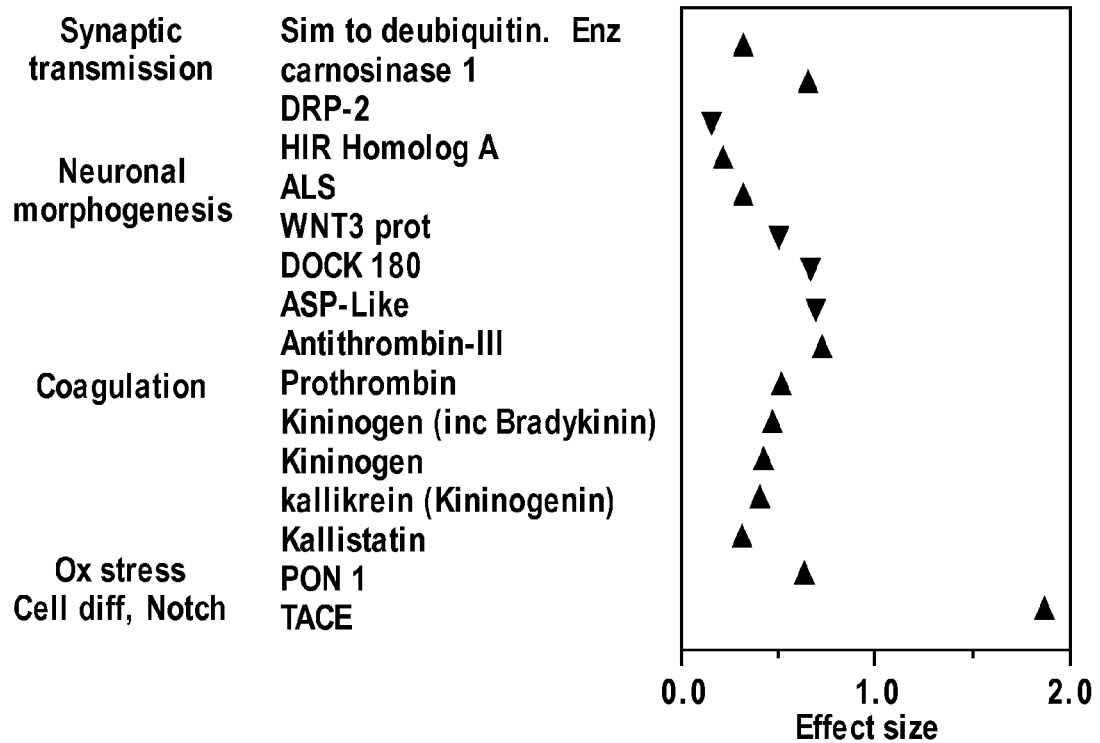
FIG. 10. Effect size for some components that are different between the Autism and Normal groups. Effect size is the Mean Difference between the two groups divided by the weighted standard deviation. ▲ Up in Autism, ▼ Down in Autism. An effect size of 0.5 is modest, 1.0 strong and 2.0 very strong.

Linking to a peptide library database and additional directed tandem mass spectrometry has identified a large fraction of the components. Overall 61% of the components have been identified, with a larger fraction among those with the lowest p-values (Table 14). This corresponds to 576 different accession numbers (approximately equal to proteins) represented by 2169 peptides. There are two or more peptides for 48% of the proteins (FIG. 9). This is useful for evaluating consistent results.

TABLE 12

Comparison of select CD8 T Cell Subsets

| ID | Cell Population | Var | Normal (N = 35) | HFA (N = 35) | LFA (N = 35) | Trend | Univariate P-value* |
|---|---|---|---|---|---|---|---|
| 3690 | CD26 negative | Ct | 322 (182) | 469 (257) | 501 (298) | ↑ | 0.01002 |
| 3691 | CD26 negative/CD8 T cells | Ct | 51.1% (24) | 72.3% (25) | 69.3% 28) | ↑ | 0.00110 |
| 3692 | CD26 positive | Ct | 323 (234) | 176 (183) | 209 (217) | ↓ | 0.00162 |
| 3693 | CD26 positve/CD8 T cells | Ct | 48.9% (24) | 27.7% (25) | 30.6% (28) | ↓ | 0.00110 |
| 3802 | CD38 negative | Ct | 96 (117) | 175 (184) | 240 (212) | ↑ | 0.0007 |
| 3803 | CD38 negative/CD8 T cells | Ct | 14.9% (16) | 27.6% (23) | 32.5% (21) | ↑ | 0.0016 |
| 3804 | CD38 positive | Ct | 553 (272) | 476 (247) | 463 (190) | — | 0.4314 |
| 3805 | CD38 positve/CD8 T cells | Ct | 85.0% (16) | 72.3% (22) | 67.5% (21) | ↓ | 0.0016 |

*p-values are shown for the Autism vs Normal comparison

Mass Spectrometry Results

Proteomics

For this data set, there were 6348 components quantified at an occurrence threshold of 25%. An occurrence threshold of 25% means that the component had to appear in at least 25% of the samples to be reported. Each component is a distinct molecular ion, and their tally does not include all the observed

TABLE 13

Summary Statistics for Serum Proteome

| P-Value | Chance* | A vs N | HFA vs N | LHA vs N | LFA vs HFA |
|---|---|---|---|---|---|
| P < 0.001 | 6 | 52 | 7 | 15 | 6 |
| P < 0.005 | 32 | 170 | 27 | 46 | 36 |

TABLE 13-continued

Summary Statistics for Serum Proteome

| P-Value | Chance* | A vs N | HFA vs N | LHA vs N | LFA vs HFA |
|---|---|---|---|---|---|
| P < 0.01 | 64 | 301 | 55 | 87 | 82 |
| P < 0.05 | 317 | 872 | 322 | 438 | 434 |

*If variables are independent

TABLE 14

Identified Serum Proteome Components

| P-Value | Components | Number with ID | % with ID |
|---|---|---|---|
| P < 0.001 | 52 | 36 | 69 |
| P < 0.005 | 170 | 113 | 66 |
| P < 0.01 | 301 | 204 | 68 |
| P < 0.05 | 872 | 566 | 65 |
| All | 6348 | 3895 | 61 |

Comparative Results

Table 15 lists proteins found in this study that show a significant differential expression between Autistic and Normal children. The list is limited to proteins with two or more peptides that track together. Evaluating multiple peptides from the same protein is used to confirm specific differences. Proteins with the most components (peptides) are generally the most abundant in serum. There is a strong representation of proteins made in the liver, the major source of serum proteins. Highly represented biological pathways include lipid metabolism, coagulation and complement.

Figure 11:
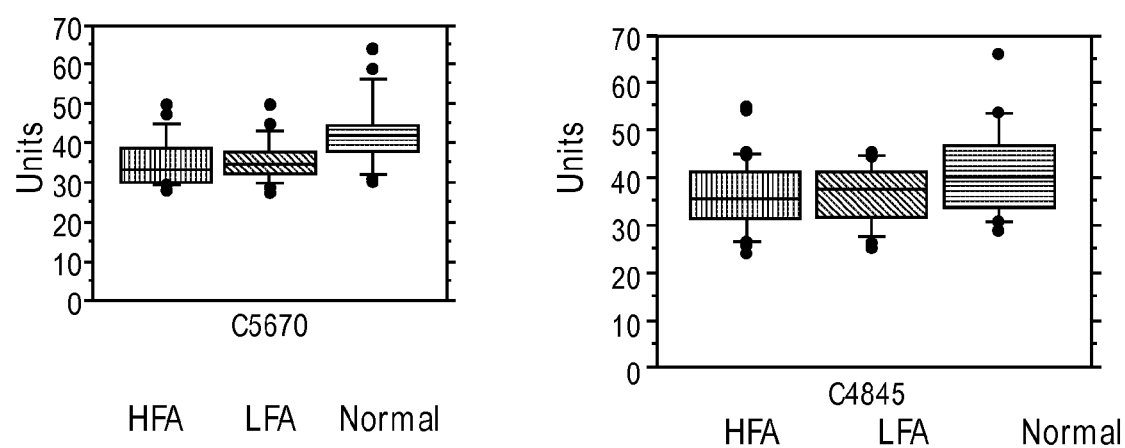
FIG. 11. Apolipoprotein B is lower in children with Autism. Right Peptide 1—SEILAHWSPAK (SEQ ID NO:4). Left: Peptide 2—GIISALLVPPETEEAK (SEQ ID NO:16). Both have p<0.001 for the Autism vs Normal comparisons. HFA (vertical lines), LFA (diagonal lines), Normal (horizontal lines). Component ID is given at the bottom of each plot.

Table 16 lists exemplified proteins tracked with single peptides that show a significant differential expression between the Autism and Normal groups. These proteins represent a more diverse set of biological processes. Some relevant themes that arise include neuronal morphogenesis and synaptic transmission. FIG. 11 plots effect size for some variable grouped by them.

TABLE 15

Listing of the most definitive changing proteins differentiating Autistic and Normal Children. Proteins with two or more consistent peptides are shown in this table.

| Accession # | gi # | Protein Description | # Components | # Peptides | <Exp Ratio> | Fold Change | Trend | Min P | <Score> |
|---|---|---|---|---|---|---|---|---|---|
| LPHUB | 71789 | apolipoprotein B-100 precursor - human | 71 | 51 | 0.96 | -1.04 | Down | 3.72E-07 | 63 |
| P02787 | 13619 | Serotransferrin precursor (Transferrin) | 29 | 20 | 1.40 | 1.40 | Up | 2.29E-03 | 79 |
| P43652 | 1168366 | Afamin precursor (Alpha-albumin) (Alpha-Alb) | 17 | 14 | 1.20 | 1.20 | Up | 4.64E-04 | 57 |
| KUHU | 1070458 | ferroxidase (EC 1.16.3.1) precursor | 15 | 11 | 0.95 | -1.05 | Down | 2.25E-04 | 70 |
| P00734 | 135807 | Prothrombin precursor (Coagulation factor II) | 12 | 10 | 1.13 | 1.13 | Up | 3.67E-06 | 68 |
| Q14624 | 13432192 | Inter-alpha-trypsin inhibitor heavy chain H4 precursor | 10 | 10 | 0.96 | -1.05 | Down | 4.74E-03 | 57 |
| P08697 | 112907 | Alpha-2-antiplasmin precursor | 10 | 9 | 1.18 | 1.18 | Up | 3.98E-05 | 56 |
| P01008 | 113936 | Antithrombin-III precursor (ATIII) (PRO0309) | 12 | 9 | 1.23 | 1.23 | Up | 1.04E-04 | 67 |
| NP_000030.1 | 4557321 | apolipoprotein A-I precursor [Homo sapiens] | 10 | 9 | 1.11 | 1.11 | Up | 3.95E-04 | 58 |
| P02647 | 113992 | Apolipoprotein A-I precursor (Apo-AI) | 10 | 8 | 1.30 | 1.30 | Up | 3.99E-03 | 80 |
| P02790 | 1708182 | Hemopexin precursor (Beta-1B-glycoprotein) | 11 | 8 | 1.16 | 1.16 | Up | 1.36E-04 | 62 |
| NP_001054.1 | 4557871 | transferrin [Homo sapiens] | 10 | 8 | 1.37 | 1.37 | Up | 1.46E-03 | 42 |
| P01011 | 112874 | Alpha-1-antichymotrypsin precursor (ACT) | 7 | 7 | 0.99 | -1.01 | Down | 4.13E-04 | 69 |
| P19823 | 125000 | Inter-alpha-trypsin inhibitor heavy chain H2 precursor | 8 | 7 | 1.09 | 1.09 | Up | 1.01E-03 | 50 |
| NP_001701.1 | 4502397 | complement factor B preproprotein; B-factor | 8 | 7 | 0.99 | -1.01 | Down | 4.82E-03 | 50 |
| KGHUL1 | 68786 | kininogen, LMW precursor [validated] - human | 6 | 6 | 1.18 | 1.18 | Up | 2.34E-03 | 83 |
| P04114 | 114014 | Apolipoprotein B-100 precursor (Apo B-100) | 6 | 6 | 0.94 | -1.06 | Down | 1.62E-02 | 60 |
| NP_000005.1 | 4557225 | alpha 2 macroglobulin precursor [Homo sapiens] | 8 | 6 | 1.17 | 1.17 | Up | 2.17E-03 | 46 |
| P08603 | 116131 | Complement factor H precursor (H factor 1) | 6 | 5 | 1.17 | 1.17 | Up | 2.51E-03 | 49 |
| P01042 | 125507 | Kininogen precursor (Alpha-2-thiol proteinase inhibitor | 6 | 5 | 1.16 | 1.16 | Up | 1.99E-04 | 48 |
| NP_002206.1 | 4504781 | inter-alpha (globulin) inhibitor, H1 polypeptide | 6 | 5 | 1.09 | 1.09 | Up | 1.03E-02 | 110 |
| P02652 | 114000 | Apolipoprotein A-II precursor (Apo-AII) | 4 | 4 | 1.22 | 1.22 | Up | 9.31E-05 | 70 |
| P02649 | 114039 | Apolipoprotein E precursor (Apo-E) | 4 | 4 | 1.14 | 1.14 | Up | 1.17E-03 | 79 |
| P00450 | 116117 | Ceruloplasmin precursor (Ferroxidase) | 6 | 4 | 0.94 | -1.06 | Down | 5.82E-03 | 75 |
| P05546 | 123055 | Heparin cofactor II precursor (HC-II) | 4 | 4 | 1.14 | 1.14 | Up | 1.84E-05 | 51 |
| P03952 | 125184 | Plasma kallikrein precursor | 4 | 4 | 0.98 | -1.02 | Down | 6.01E-04 | 56 |
| JX0368 | 1082547 | inter-alpha-trypsin inhibitor heavy chain-related protein | 4 | 4 | 1.27 | 1.27 | Up | 1.39E-02 | 77 |
| NP_001613.1 | 4502005 | alpha-2-HS-glycoprotein; Alpha-2HS-glycoprotein | 7 | 4 | 1.15 | 1.15 | Up | 1.92E-02 | 85 |
| P02765 | 112910 | Alpha-2-HS-glycoprotein precursor (Fetuin-A) | 5 | 3 | 1.09 | 1.09 | Up | 4.08E-04 | 71 |
| P06727 | 114006 | Apolipoprotein A-IV precursor (Apo-AIV) | 4 | 3 | 1.20 | 1.20 | Up | 7.94E-03 | 70 |
| P04004 | 139653 | Vitronectin precursor (Serum spreading factor) | 3 | 3 | 1.02 | 1.02 | Up | 8.97E-03 | 57 |
| P02675 | 399492 | Fibrinogen beta chain precursor | 5 | 3 | 1.17 | 1.17 | Up | 1.85E-03 | 60 |
| P02748 | 1352108 | Complement component C9 precursor | 4 | 3 | 1.02 | 1.02 | Up | 1.67E-02 | 62 |
| P02751 | 2506872 | Fibronectin precursor (FN) (Cold-insoluble globulin) | 6 | 3 | 1.19 | 1.19 | Up | 1.29E-02 | 69 |
| NP_000884.1 | 4504893 | kininogen [Homo sapiens] | 4 | 3 | 1.05 | 1.05 | Up | 5.18E-03 | 79 |
| NP_000574.1 | 9845255 | group-specific component (vitamin D binding protein) | 3 | 3 | 1.16 | 1.16 | Up | 9.07E-03 | 51 |

TABLE 15-continued

Listing of the most definitive changing proteins differentiating Autistic and Normal Children. Proteins with two or more consistent peptides are shown in this table.

| Accession # | gi # | Protein Description | # Components | # Peptides | <Exp Ratio> | Fold Change | Trend | Min P | <Score> |
|---|---|---|---|---|---|---|---|---|---|
| NP_005132.1 | 11761631 | fibrinogen, beta chain preproprotein [Homo sapiens] | 3 | 3 | 1.10 | 1.10 | Up | 1.18E−03 | 48 |
| NP_002017.1 | 16933542 | fibronectin 1 isoform 1 preproprotein | 3 | 3 | 1.16 | 1.16 | Up | 1.22E−02 | 50 |
| NP_006112.2 | 17318569 | keratin 1; Keratin-1; cytokeratin 1 | 3 | 3 | 1.12 | 1.12 | Up | 6.18E−03 | 37 |
| NP_001822.2 | 42716297 | clusterin isoform 1; complement-associated protein | 3 | 3 | 1.15 | 1.15 | Up | 1.15E−02 | 37 |
| P02763 | 112877 | Alpha-1-acid glycoprotein 1 precursor (AGP 1) | 2 | 2 | 0.95 | −1.05 | Down | 5.13E−03 | 47 |
| P01019 | 113880 | Angiotensinogen precursor | 2 | 2 | 1.16 | 1.16 | Up | 5.00E−03 | 48 |
| P00742 | 119761 | Coagulation factor X precursor (Stuart factor) | 2 | 2 | 1.04 | 1.04 | Up | 5.58E−03 | 40 |
| P04196 | 123523 | Histidine-rich glycoprotein precursor | 2 | 2 | 0.91 | −1.10 | Down | 3.43E−03 | 56 |
| P01871 | 127514 | Ig mu chain C region | 3 | 2 | 1.21 | 1.21 | Up | 1.34E−02 | 71 |
| P02766 | 136464 | Transthyretin precursor (Prealbumin) (TBPA) | 3 | 2 | 1.00 | −1.00 | Down | 1.65E−02 | 57 |
| P19652 | 231458 | Alpha-1-acid glycoprotein 2 precursor (AGP 2) | 3 | 2 | 0.90 | −1.11 | Down | 1.96E−03 | 57 |
| P35858 | 543800 | Insulin-like growth factor binding protein complex | 2 | 2 | 1.14 | 1.14 | Up | 6.3E−03 | 45 |
| Q03591 | 543981 | Complement factor H-related protein 1 precursor | 2 | 2 | 1.38 | 1.38 | Up | 2.28E−03 | 73 |
| P35542 | 548885 | Serum amyloid A-4 protein precursor | 3 | 2 | 1.19 | 1.19 | Up | 9.39E−03 | 49 |
| P02671 | 1706799 | Fibrinogen alpha/alpha-E chain precursor | 2 | 2 | 0.98 | −1.02 | Down | 1.17E−02 | 59 |
| P29622 | 1708609 | Kallistatin precursor (Kallikrein inhibitor) | 2 | 2 | 1.13 | 1.13 | Up | 4.54E−03 | 41 |
| ANHU | 2144576 | angiotensin precursor [validated] - human | 2 | 2 | 1.02 | 1.02 | Up | 9.42E−03 | 40 |
| P19827 | 2851501 | Inter-alpha-trypsin inhibitor heavy chain H1 precursor | 2 | 2 | 1.04 | 1.04 | Up | 1.44E−02 | 59 |
| NP_001124.1 | 4501987 | afamin precursor; alpha-albumin [Homo sapiens] | 2 | 2 | 1.14 | 1.14 | Up | 4.54E−03 | 30 |
| NP_000473.1 | 4502151 | apolipoprotein A-IV precursor [Homo sapiens] | 2 | 2 | 1.30 | 1.30 | Up | 6.00E−03 | 59 |
| NP_000604.1 | 11321561 | hemopexin [Homo sapiens] | 2 | 2 | 0.95 | −1.05 | Down | 2.90E−02 | 48 |
| O95445 | 17370872 | Apolipoprotein M (Apo-M) (ApoM) (G3a) | 2 | 2 | 1.16 | 1.16 | Up | 7.84E−04 | 48 |

TABLE 16

Listing of additional changing proteins differentiating Autistic and Normal Children. A subset of proteins identified with a single peptide is shown in this table.

| Accession # | Protein Description | # Components | # Peptides | <Exp Ratio> | Fold Change | Trend | P | <Score> |
|---|---|---|---|---|---|---|---|---|
| RWHU1B | Cell surface glycoprotein CD11b precursor [validated] | 1 | 1 | 0.95 | −1.05 | Down | 4.2E−02 | 28 |
| P00505 | Aspartate aminotransferase, mitochondrial precursor | 1 | 1 | 0.90 | −1.11 | Down | 3.2E−02 | 36 |
| P08185 | Corticosteroid-binding globulin precursor (CBG) | 1 | 1 | 1.12 | 1.12 | Up | 1.6E−02 | 56 |
| P22792 | Carboxypeptidase N 83 kDa chain | 1 | 1 | 1.20 | 1.20 | Up | 2.5E−02 | 54 |
| P05108 | Cytochrome P450 11A1, mitochondrial precursor | 2 | 1 | 1.06 | 1.06 | Up | 9.1E−03 | 27 |
| P27169 | Serum paraoxonase/arylesterase 1 (PON 1) | 2 | 1 | 1.29 | 1.29 | Up | 7.0E−03 | 45 |
| P07225 | Vitamin K-dependent protein S precursor | 1 | 1 | 0.94 | −1.06 | Down | 9.6E−03 | 35 |
| S23386 | Protein kinase (EC 2.7.1.37) cdc2-related PSSALRE | 1 | 1 | 1.09 | 1.09 | Up | 3.6E−02 | 27 |
| A47536 | WNT3 protein - human | 1 | 1 | 0.89 | −1.12 | Down | 3.5E−02 | 34 |
| P35527 | Keratin, type I cytoskeletal 9 (Cytokeratin 9) (K9) (CK 9) | 1 | 1 | 0.88 | −1.13 | Down | 1.7E−02 | 74 |
| P07357 | Complement component C8 alpha chain precursor | 1 | 1 | 0.96 | −1.04 | Down | 2.2E−02 | 76 |
| A47161 | Mac-2-binding glycoprotein precursor - human | 1 | 1 | 1.18 | 1.18 | Up | 2.6E−02 | 32 |
| P48547 | Potassium voltage-gated channel subfamily C member 1 | 1 | 1 | 1.15 | 1.15 | Up | 3.5E−02 | 47 |
| Q00610 | Clathrin heavy chain 1 (CLH-17) | 1 | 1 | 0.99 | −1.01 | Down | 3.9E−02 | 26 |
| P49908 | Selenoprotein P precursor | 1 | 1 | 1.07 | 1.07 | Up | 2.1E−02 | 94 |
| A38194 | desmoplakin I - human | 1 | 1 | 0.89 | −1.12 | Down | 1.2E−02 | 32 |
| Q14566 | DNA replication licensing factor MCM6 (P105MCM) | 1 | 1 | 1.29 | 1.29 | Up | 3.3E−02 | 33 |
| Q16610 | Extracellular matrix protein 1 precursor | 1 | 1 | 0.96 | −1.04 | Down | 1.5E−03 | 39 |
| Q14999 | Cullin homolog 7 (CUL-7) | 1 | 1 | 1.08 | 1.08 | Up | 2.7E−02 | 37 |
| Q16555 | Dihydropyrimidinase related protein-2 (DRP-2) | 1 | 1 | 0.92 | −1.08 | Down | 2.6E−02 | 28 |
| NP_000479.1 | serine (or cysteine) proteinase inhibitor, clade C | 2 | 1 | 1.09 | 1.09 | Up | 7.9E−03 | 50 |
| NP_000345.1 | serine (or cysteine) proteinase inhibitor, clade A | 1 | 1 | 0.88 | −1.14 | Down | 8.0E−05 | 59 |
| Q14324 | Myosin-binding protein C, fast-type (Fast MyBP-C) | 1 | 1 | 1.14 | 1.14 | Up | 7.8E−03 | 31 |
| O60241 | Brain-specific angiogenesis inhibitor 2 precursor | 1 | 1 | 0.93 | −1.07 | Down | 2.4E−02 | 28 |
| NP_003390.2 | X-prolyl aminopeptidase 2, membrane-bound | 1 | 1 | 1.24 | 1.24 | Up | 9.0E−03 | 29 |
| NP_068604.1 | a disintegrin and metalloproteinase domain 17 isoform 2 | 1 | 1 | 1.48 | 1.48 | Up | 4.9E−04 | 27 |
| NP_057427.2 | centromere protein F (350/400 kD); mitosin | 1 | 1 | 0.92 | −1.08 | Down | 2.4E−02 | 29 |
| Q14161 | ARF GTPase-activating protein GIT2 | 1 | 1 | 0.97 | −1.03 | Down | 1.9E−02 | 27 |
| Q9NZJ5 | Eukaryotic translation initiation factor 2-alpha kinase 3 precursor | 1 | 1 | 1.26 | 1.26 | Up | 5.9E−04 | 30 |
| NP_000437.3 | paraoxonase 1; Paraoxonase [Homo sapiens] | 1 | 1 | 0.92 | −1.09 | Down | 3.9E−02 | 36 |
| NP_005656.2 | ecotropic viral integration site 5; Neuroblastoma stage 4S gene | 1 | 1 | 1.17 | 1.17 | Up | 2.2E−02 | 26 |
| NP_116038.4 | carnosinase 1; glutamate carboxypeptidase-like protein 2 | 1 | 1 | 0.95 | −1.06 | Down | 2.0E−02 | 25 |

TABLE 16-continued

Listing of additional changing proteins differentiating Autistic and Normal Children.
A subset of proteins identified with a single peptide is shown in this table.

| Accession # | Protein Description | # Components | # Peptides | <Exp Ratio> | Fold Change | Trend | P | <Score> |
|---|---|---|---|---|---|---|---|---|
| NP_002617.2 | phosphofructokinase, liver; Phosphofructokinase, liver type; | 1 | 1 | 0.84 | -1.19 | Down | 1.2E-03 | 27 |
| NP_443122.2 | peptidoglycan recognition protein L precursor [Homo sapiens] | 1 | 1 | 1.14 | 1.14 | Up | 6.1E-03 | 75 |
| NP_071354.2 | hypothetical protein FLJ20967 [Homo sapiens] | 1 | 1 | 0.94 | -1.06 | Down | 3.1E-02 | 31 |
| NP_003316.3 | HIR (histone cell cycle regulation defective, S. cerevisiae) | 1 | 1 | 1.10 | 1.10 | Up | 3.2E-02 | 37 |
| NP_060606.2 | asp (abnormal spindle)-like, microcephaly associated | 1 | 1 | 0.92 | -1.09 | Down | 4.6E-02 | 42 |
| Q14185 | Dedicator of cytokinesis protein 1 (180 kDa protein) | 1 | 1 | 0.84 | -1.19 | Down | 2.4E-05 | 26 |

Specific Differences

A select set of peptide differences are presented in box and whisker plots in FIGS. 11 to 15. Selections are based on p-values for the Autism vs Normal Comparison, however distributions are presented by for HFA, LFA and Normal groups.

Apolipoprotein B. (Apo B) is the major protein component of all lipoproteins other than HDL. It functions as a recognition signal for the cellular binding and internalization of LDL particles by the Apo B/E receptor. Many apolipoprotein B peptides are significantly lower in children with Autism (FIG. 11). The LFA and HFA groups are not different for these peptides.

Figure 12:
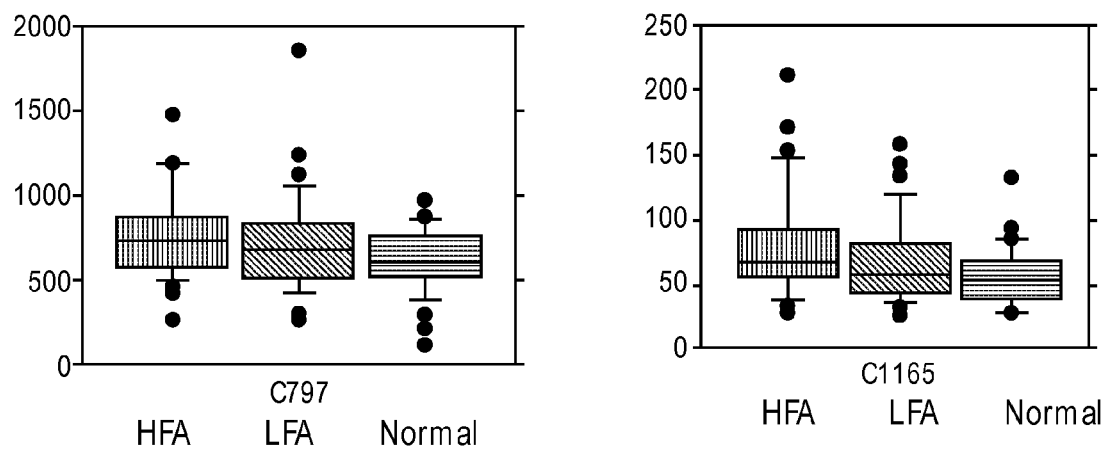
FIG. 12. Transferrin is higher in children with Autism. Right Peptide 1—SDNCEDTPEAGYFAVAVVK (SEQ ID NO:17). Left: Peptide 2—v. Both have p<0.01 for the Autism vs Normal comparisons. HFA (vertical lines), LFA (diagonal lines), Normal (horizontal lines). Component ID is given at the bottom of each plot.

Transferrin is the major iron transport protein in serum. Many transferrin peptides are higher in children with Autism (FIG. 12). The protein is identified with two accession numbers, P02787 and NP_001054.1.

Figure 13:
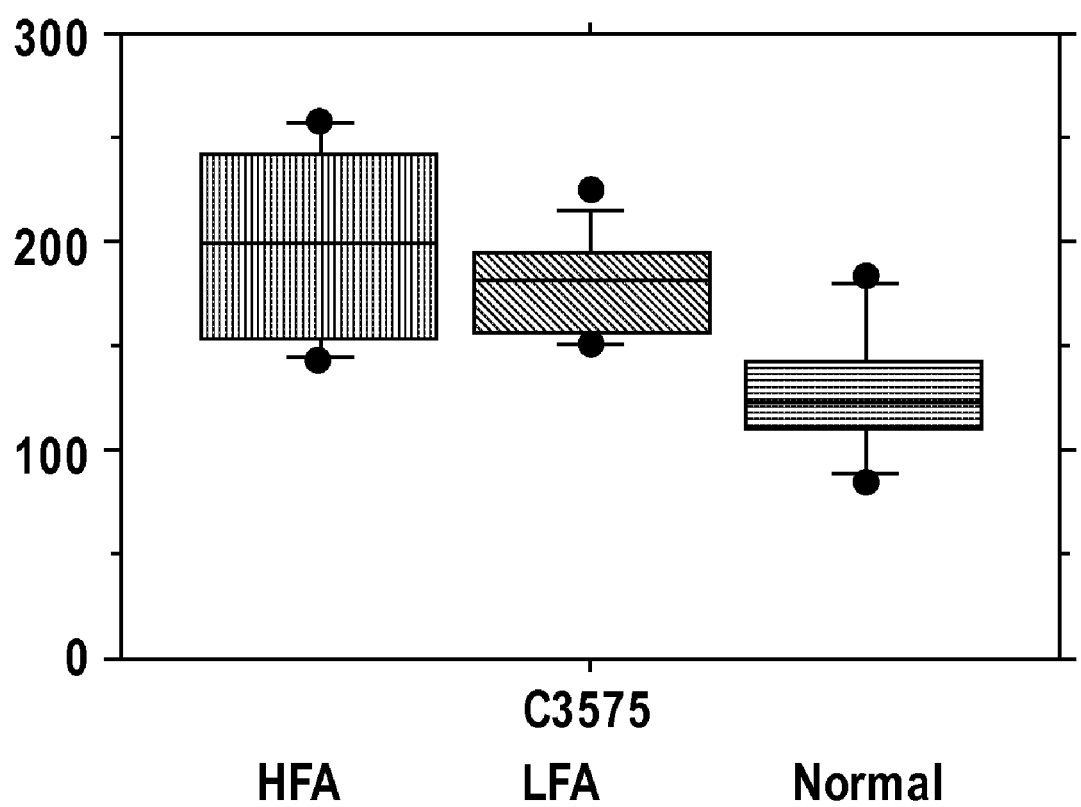
FIG. 13. Peptide with greatest effect size is higher in children with Autism. The peptide ID is TNFα converting enzyme. P<0.001 for the Autism vs Normal comparisons. HFA (vertical lines), LFA (diagonal lines), Normal (horizontal lines). Component ID is given at the bottom of the plot. Peptide=MLVYK (SEQ ID NO:1). Effect size 1.9. Effect size is the Mean Difference between the two groups divided by the weighted standard deviation.

Peptide with greatest effect size has been identified as from the TNFα converting enzyme (TACE). It is significantly higher in children with Autism (FIG. 13). This protein is normally a membrane bound (CD156b). It is responsible for cleaving the membrane-bound precursor of TNFα to its mature soluble form. It appears to shed a number of other proteins as well. This appears to be the first evidence of a soluble form of this protein. The peptide is short, five amino acids, and has a modest MASCOT ID score, 27. In addition it is only above threshold in about 30% of the samples.

Figure 14:
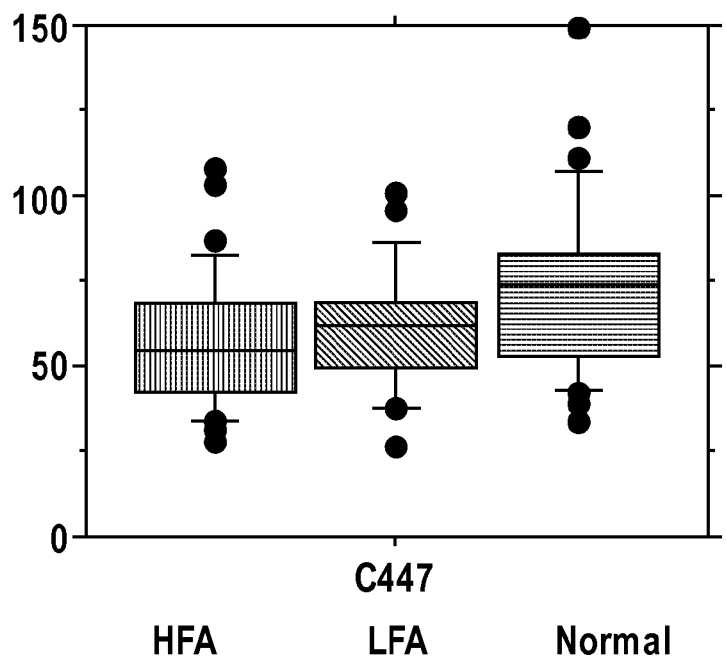
FIG. 14. DOCK180 is lower in children with Autism. P<0.001 for the Autism vs Normal comparisons. HFA (vertical lines), LFA (diagonal lines), Normal (horizontal lines). Component ID is given at the bottom of the plot.

Dock 180, dedicator of cytokinesis protein 1, plays a key role in development, cell motility and phagocytosis. There is one peptide with this identification and it is lower in children with Autism (FIG. 14).

Figure 15:
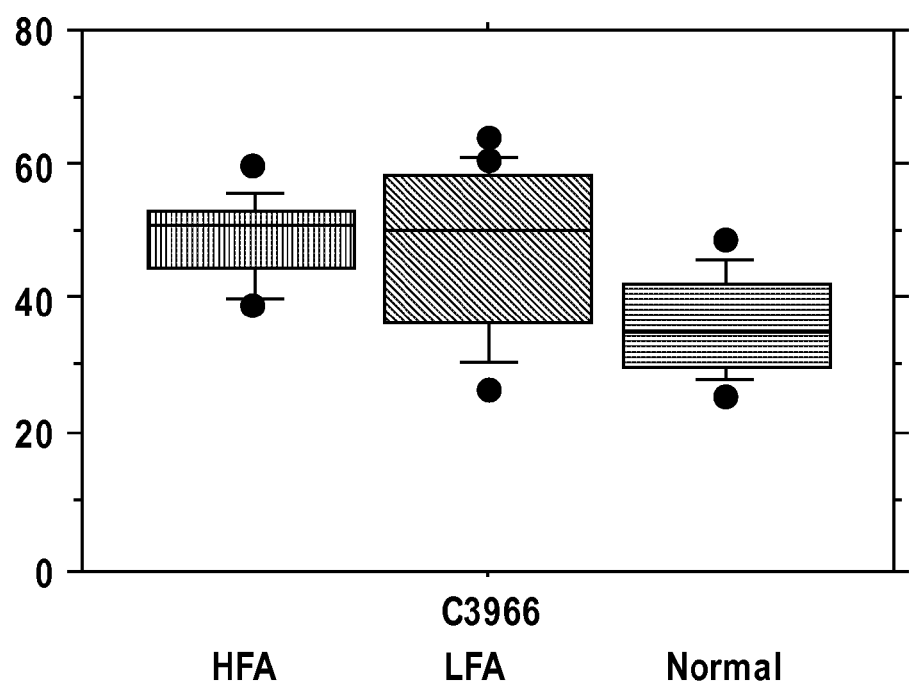
FIG. 15. Complement factor H-related protein 1 (FHR1) peptide is higher in children with Autism. P<0.01, effect size=1.4 for the Autism vs Normal comparisons. HFA (vertical lines), LFA (diagonal lines), Typical (horizontal lines). Component ID is given at the bottom of the plot. Peptide=TGESAEFVCK (SEQ ID NO:2.
Figure 16:
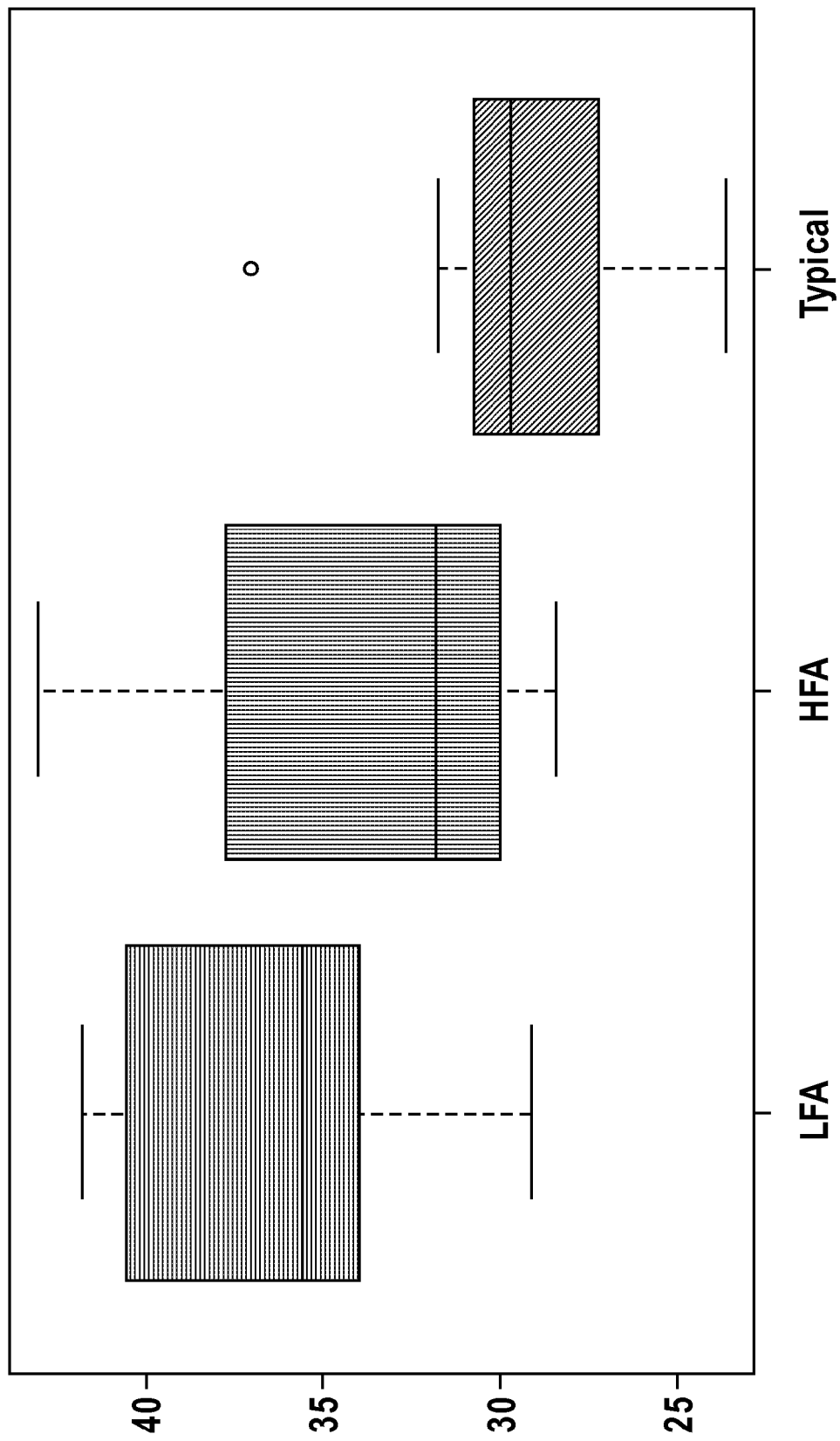
FIG. 16. Complement C1q subcomponent: C chain peptide is higher in children with Autism. Complement C1q subcomponent: C chain precursor concentrations in children with low functioning autism (LFA (horizontal lines )) and high functioning autism (HFA (vertical lines)) compared to typical developing, normal children (Typical (diagonal lines)). The peptide sequence used to identify this protein, the Accession Number, p value and effect size are given in Table 17. Peptide=FNAVLTNPQGDYDTSTGK (SEQ ID NO:6).

Complement factor H-related protein (FHR1) is higher in children with Autism (FIG. 15). The protein may play a role in complement regulation. It can associate with lipoproteins and may play a role in lipid metabolism. Effect size for this peptide is 1.4 as reflected in the good separation between the groups. An additional peptide from this protein was also higher at a p-value<0.01. The peptides were above threshold in about 40% of samples.

Table 17 shows proteins/peptides regulated in the serum of children with autism compared to age, race and gender matched controls. These proteins were significantly different in autism (n=70) compared to typical children (n=35) p<0 01, unpaired t-test) and had an effect size of 1 or more. Down (−) means decrease in serum of children with autism compared to typical children.

Figure 17:
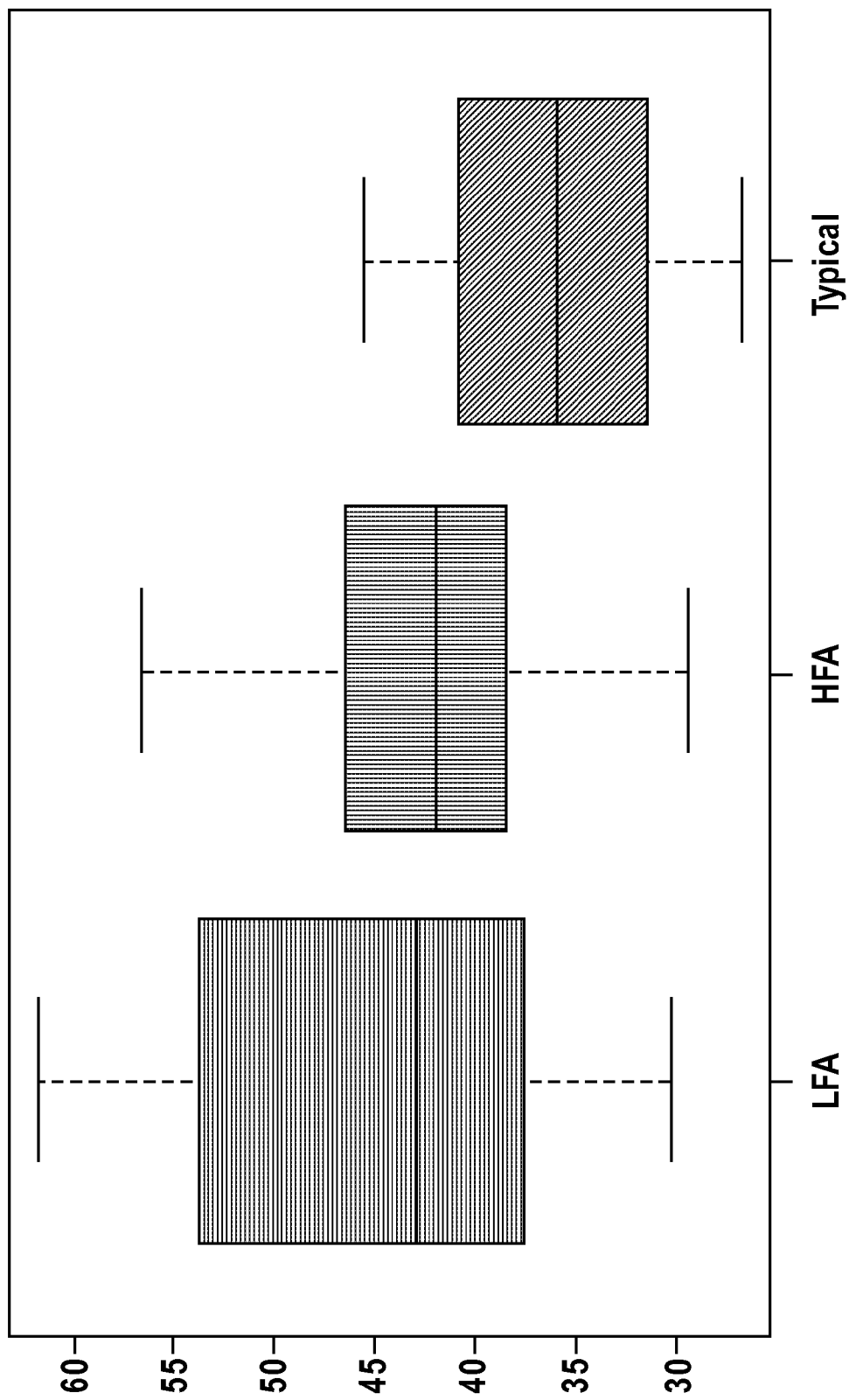
FIG. 17. Fibronectin 1 isoform 1 peptide is higher in children with Autism. Fibronectin 1 isoform 1 preprotein concentrations in children with low functioning autism (LFA (horizontal lines)) and high functioning autism (HFA (vertical lines)) compared to typical developing, normal children (Normal, (diagonal lines)). The peptide sequence used to identify this protein, the Accession Number, p value and effect size are given in Table 17. Peptide=NLQPASEYTVSLVAIK (SEQ ID NO:7).
Figure 18:
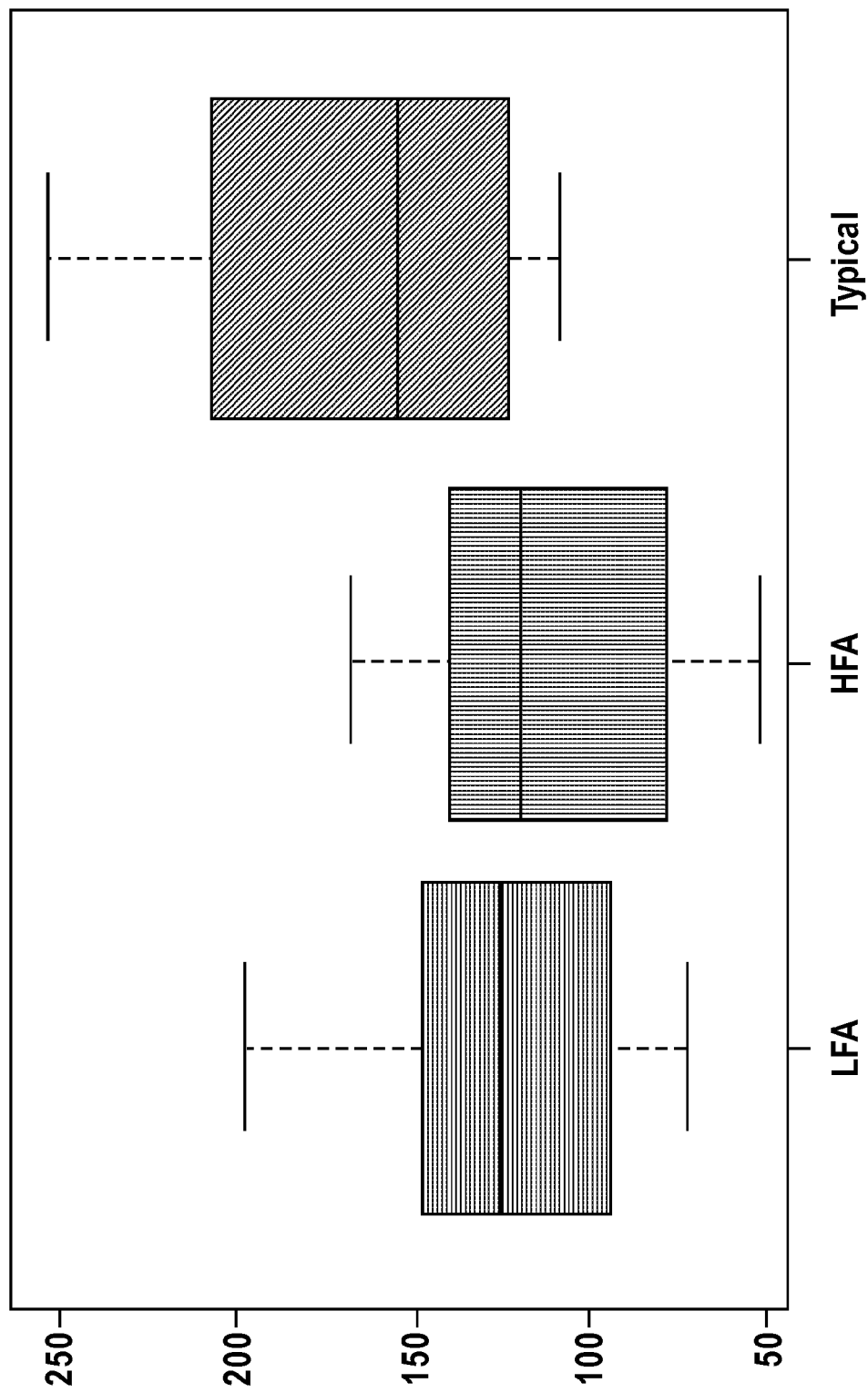
FIG. 18. Complement component 4B peptide is lower in children with Autism. Complement component 4B proprotein concentrations in children with low functioning autism (LFA (horizontal lines )) and high functioning autism (HFA (vertical lines)) compared to typical developing, normal children (Typical (diagonal lines)). The peptide sequence used to identify this protein, the Accession Number, p value and effect size are given in Table 17. Peptide=EPFLSCCQFAESLR (SEQ ID NO:8).
Figure 19:
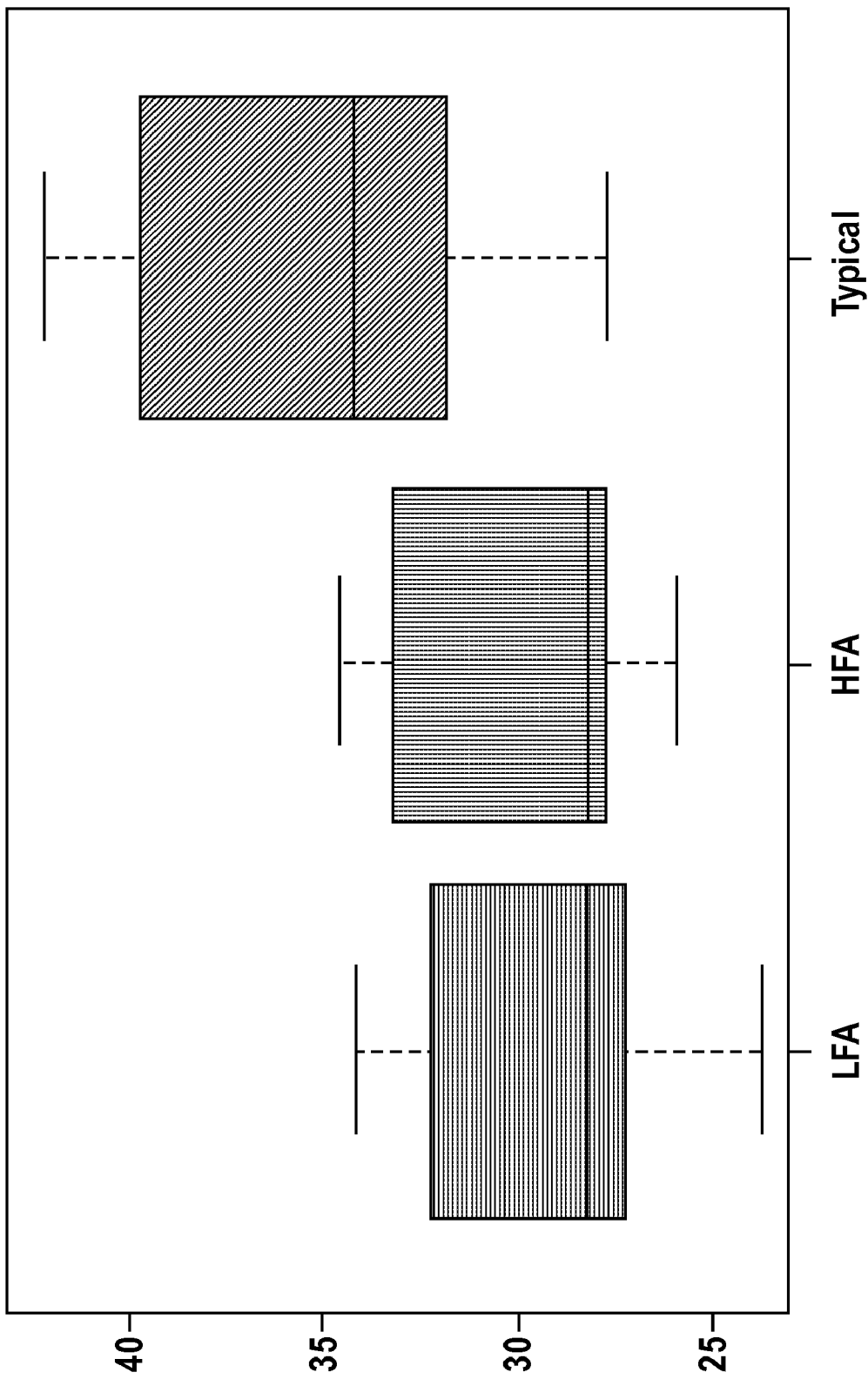
FIG. 19. Complement component 3 peptide is lower in children with Autism. Complement component 3 precursor concentrations in children with low functioning autism (LFA (horizontal lines )) and high functioning autism (HFA (vertical lines)) compared to typical developing, normal children (Typical (diagonal lines)). The peptide sequence used to identify this protein, the Accession Number, p value and effect size are given in Table 17. Peptide=KGYTQQLAFRQPSSAFAAFVK (SEQ ID NO:3).

A number of these proteins were related to the complement system (FIGS. 15-20). The C Chain precursor of the Complement C 1 q subcomponent was up regulated (FIG. 16), as was Fibronectin 1 isoform 1 preprotein (FIG. 17). Complement factor-H-related protein 1 precursor (FHR-1) (FIGS. 15 and 20) was also up regulated in serum of children with autism compared with normal controls. FIGS. 15 and 20 show two different peptides from the same FHR-1 protein, and show similar elevations in autism compared to the typically developing controls.

Complement component 4B proprotein (FIG. 18) and complement component 3 precursor protein (FIG. 19) were decreased in the serum of children with autism compared to typically developing controls. Apolipoprotein B-100 precursor was decreased in serum of children with autism compared to normal controls (FIG. 11). This protein was identified by ten peptides.

The peptide with the largest effect size in the study is MLVYK (SEQ ID NO:1) (FIG. 13), which is significantly higher in serum of children with autism compared to controls. This protein was found on a BLAST search to occur in two unrelated proteins: TNFα converting enzyme (TACE) and in the familial breast cancer related protein (BRCA1). Since there were no other peptides identified in TACE or BRCA1, it is unclear whether the protein represented by this peptide is TACE or BRCA1 and therefore is labeled as such (FIG. 8).

Table 18 shows proteins/peptides regulated in the serum of children with autism with low functioning autism (LFA) compared to those with high functioning autism (HFA). These proteins were significantly different between LFA (n=34) compared to HFA (n=34) (p<0.05, paired t-test) and had an effect size of 1 or more. Down (−) indicates a decrease in serum of children with HFA compared to LFA.

The concentrations of the listed proteins were higher in the serum of children with LFA compared to HFA. One of the peptides identifies a protein, apolipoprotein B-100 that is also decreased and on the list of proteins that differentiate autism from typically developing children and was identified by nine peptides (Table 17).

Additional peptides related to the complement family were also differentially expressed in LFA versus HFA but are not included in Table 18. These peptides are related to the following known proteins: Complement C1r component precursor, Complement component C9 precursor, Complement component C8 beta chain precursor, Clusterin isoform 1 or complement-associated protein SP-40, Complement factor I precursor, C3B/C4B inactivator, fibronectin precursor, and nuclear receptor coactivator 4 (NCoA-4) (70 kDa androgen receptor co-activator).

TABLE 17

Peptides/Proteins Significantly Changed In Children With Autism Compared To Normal Children

| Accession Number | Protein Description | Peptide (SEQ ID NO:) | P-value | Fold Change | Effect Size | # Peptides with p < 0.05 |
|---|---|---|---|---|---|---|
| NP_068604.1 | TNF-alpha converting enzyme (TACE) or BRCA1 protein | MLVYK (1) | 0.00003 | 1.48 | 1.82 | 1 |
| Q03591 | Complement factor H-related protein 1 precursor (FHR-1) | TGESAEFVCK (2) | 0.00005 | 1.33 | 1.33 | 2 |
| NP_000055.1 | Complement component 3 precursor | KGYTQQLAFRQPSSAFAAFVK (3) | 0.002 | −1.22 | −1.52 | 1 |
| LPHUB | Apolipoprotein B-100 precursor | SEILAHWSPAK (4) | 0.001 | −1.20 | −1.06 | 10 |
| Q03591 | Complement factor H-related protein 1 precursor (FHR-1) (H factor-like protein 1) | ITCTEEGWSPTPK (5) | 0.005 | 1.26 | 0.99 | 2 |
| P02747 | Complement C1q subcomponent, C chain precursor | FNAVLTNPQGDYDTSTGK (6) | 0.004 | 1.19 | 1.26 | 1 |
| NP_002017.1 | Fibronectin 1 isoform 1 preproprotein; cold-insoluble globulin | NLQPASEYTVSLVAIK (7) | 0.002 | 1.23 | 1.00 | 1 |
| NP_000583.1 | Complement component 4B proprotein | EPFLSCCQFAESLR (8) | 0.02 | −1.39 | −1.07 | 1 |

TABLE 18

Peptides/Proteins Significantly Changed In Children With Low Functioning Autism Compared To Children With High Functioning Autism

| Accession Number | Protein Description | Peptide (SEQ ID NO): | P-value | Fold Change | Effect Size | # Peptides with p < 0.05 |
|---|---|---|---|---|---|---|
| NP_003541.1 | MAD1-like 1; MAD1 (mitotic arrest deficient, yeast, homolog)-like 1; mitotic-arrest deficient 1 | VLHMSLNPTSVAR (9) | 0.042 | −1.34 | −1.34 | 1 |
| LPHUB | apolipoprotein B-100 precursor | IHSGSFQSQVELSNDQEK (10) | 0.032 | −1.30 | −1.14 | 9 |
| NP_000473.1 | apolipoprotein A-IV precursor | LAPLAEDVR (11) | 0.014 | −1.16 | −1.12 | 6 |
| NP_056391.1 | cytomatrix protein p110 | ESSLIDLK (12) | 0.027 | −1.17 | −1.04 | 1 |
| P02655 | Apolipoprotein C-II precursor (Apo-CII) | TYLPAVDEK (13) | 0.016 | −1.45 | −1.01 | 1 |
| O14904 | Wnt-9a protein precursor (Wnt-14) | WNCTLEGR (14) | 0.026 | −1.38 | −0.99 | 1 |
| NP_733828.2 | WD repeat domain 17 isoform 1 | NELLILCGYIGALLAIR (15) | 0.001 | −1.31 | −0.99 | 1 |

LC-Metabolome

For this data set, there were 3741 components quantified at an occurrence threshold of 25%. The median CV's are 34% and 32% for the Autism and Normal groups respectively which is typical of other human serum metabolome studies. A summary of the significant measures for each of the comparisons is shown in Table 19. The most differences were observed in the Autism vs Normal comparison, which includes more samples (70 vs 35) than the other three comparisons (35 v 35). The number of hits that might be expected by chance, if all of the variables are independent, is also given in the table. In our experience, however, comparison of control vs. control yields half or less than what would be expected by chance at each p-value level.

TABLE 19

Summary Statistics for Serum LC-Metabolome

| P-Value | Chance | A vs N | HFA vs N | LHA vs N | LFA vs HFA |
|---|---|---|---|---|---|
| P < 0.001 | 4 | 162 | 43 | 20 | 4 |
| P < 0.005 | 19 | 271 | 112 | 79 | 21 |
| P < 0.01 | 37 | 357 | 175 | 122 | 48 |
| P < 0.05 | 197 | 693 | 426 | 395 | 228 |

Supporting Material

Cytometry Data

Fields

ASSAY is the assay name. The string consists of the target antigens separated by underscores and arranged by the channel number the reagent is measured on with SurroScan. Assay version is appended at the end. A typical study may have 10 to 100 assays.

ENTITY describes the specific cell population. Names are based on the presence (p) or absences (n) of an individual antigen, e.g. CD3pCD8p represents CD3 positive CD8 positive T cells, i.e. CD8 T cells. A typical ASSAY may have 1 to 10 different populations associated with it.

PROPERTY is the identifier of the type of statistic represented by the field VALUE such as COUNT (cells per uL) or INTENSITY (relative). Count and intensity results are typically generated for each POPULATION_NAME STAT_LEVEL output variables are classified into three statistical categories for comparative statistical analysis. (S1, S2 or S3).

S1—variable statistic—used in reduced variable set form primary analysis. Bonferroni-type corrections are applied to this set.

S2—informative statistic—biological useful representation, but may be redundant with other variables.

COHORT is the group classification identifier for the samples. LFA, HFA and N are used. A=[LFA+HFA]

TIME. Time-type for longitudinal studies. All are T00 here.

VALUE is the result for the given STATISTIC_NAME. A typical POPULATION_NAME may have 1 to 5 exported VALUES associated with it. Thus, a typical ASSAY_NAME may have 1 to 50 values associated with it.

Mass Spectrometry Result Tables

Glossary of Terms for Mass Spectrometry

| Legend/Abbreviation | Description |
| --- | --- |
| <Exp. Ratio> | Mean of expression ratios from all contributing components |
| <p> | Mean P Value |
| Accession # | Identification Number from NCBI's RefSeq Database |
| Ave. Peptide Score | Average numerical score from protein identification software matching raw data to NCBI database entries |
| Avg | Average; same as Arithmetic Mean |
| Component | A molecular ion tracked and quantified for LC-MS (one molecular ion includes all of its isotopes); separately resolved chromatographic peak for GC-MS |
| Component # | Number used to denote a given component |
| Count | Number of subjects per study group with detected intensity for a specific component |
| CountDiff | Count difference between study groups; difference between two study groups of the number of subjects reporting a detectable intensity for a given component |
| CountDiffmin | Minimum number by which 2 groups may differ in count, to be categorized as a Count Diff |
| CV | Coefficient of variation |
| DM(mD) | Difference between observed mass and theoretical mass of matched peptide (in milliDaltons) |
| DM(ppm) | Difference between observed mass and theoretical mass of matched peptide (in parts per million) |
| Exp. Ratio | Expression ratio. Mean of the ratio of paired intensities, Group 1/Group 2 |
| Fold Change | Expression change factor; Positive indicates intensity increase, (negative indicates decrease). Group 1/Group 2 |
| GC-MS | Gas Chromatography-Mass Spectrometry |
| gi # | Identification Number from NCBI's RefSeq Database |
| LC-MS | Liquid Chromatography-Mass Spectrometry |
| m/z | Mass-to-charge ratio; fundamental measure in mass spectrometry |
| M + H | Protonated parent mass |
| Mean | Arithmetic Mean |
| Median | The number in the middle of a set of numbers |
| Metab. | Metabolome |

-continued

| Legend/Abbreviation | Description |
| --- | --- |
| P or p | P value assigned to component resulting from parametric or non-parametric test, depending on test for normality |
| Peptide | Sequence of an identified peptide; All individually identified charge states for a given peptide are listed. |
| Peptide/Mass | Sequence of peptide identified or accurate mass of metabolite identified |
| Protein Description | Information on the protein identified, as contained in the NCBI queried database |
| R.T. | Chromatographic retention time |
| Score | Numerical confidence score used in peptide identification via matching to a database |
| SD | Standard Deviation |
| Trend | "Up" for increased and "Down" for decreased expression level, Group 1 relative to Group 2 |
| Z | Charge state of a molecular ion |

Example 2

This example demonstrates a correlative relationship between individuals with an autism spectrum disorder and the occurrence of familial autoimmunity.

Autism has been associated with autoimmune disorders in the proband's relatives. Comi et al. compared families of patients with autism (61 families) and healthy controls (46 families) and reported that 46% of the autism group reported having relatives with rheumatoid arthritis (RA) (Comi et al., (1999) *J Child Neurol* 14:388). Table 20 shows frequency data of family history of rheumatoid arthritis (RA), multiple sclerosis (MS) and asthma among typically developing, normal children (TYP), children with low functioning autism (LFA) and children with high functioning autism (HFA). In the current investigation 29% of the children with autism (HFA and LFA) and only 6% of the typically developing, normal children had relatives with rheumatoid arthritis (Table 20). The data support previous reports of abnormalities of various immune-related molecules in the blood of children and adults with autism.

TABLE 20

| GROUP | Family History RA | Family History MS | Family History Asthma |
| --- | --- | --- | --- |
| TYP | 2 | 0 | 7 |
| LFA | 10 | 1 | 7 |
| HFA | 10 | 2 | 10 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for diagnosing an autism spectrum disorder in an individual, said method comprising:
   a) determining the level of complement factor H-related protein (FHR1) in a blood or serum sample from a first individual exhibiting symptoms of an autism spectrum disorder; and
   b) comparing the level of the FHR1 determined in step a) with the level of the FHR1 in a control sample from a second individual or a population of individuals who do not have an autism spectrum disorder;
   wherein levels of increased complement factor H-related protein (FHR1) in the sample from the first individual in comparison to the control sample from the second individual or population of individuals is indicative of an autism spectrum disorder.

2. The method of claim 1, further comprising determining the level of one or more polypeptide markers selected from the group consisting of apolipoprotein B, transferrin, TNF-alpha converting enzyme, dedicator of cytokinesis protein 1 (DOCK 180), fibronectin 1, complement C1q, complement component 3 precursor protein, and complement component 4B proprotein, wherein levels of decreased apolipoprotein B, increased transferrin, increased TNF-alpha converting enzyme, decreased dedicator of cytokinesis protein 1 (DOCK 180), increased fibronectin 1, increased complement C1q, decreased complement component 3 precursor protein, or decreased complement component 4B proprotein in the sample from the first individual in comparison to the control sample from the second individual or population of individuals is indicative of an autism spectrum disorder.

3. The method of claim 1, further comprising determining the level of one or more immune cell markers selected from the group consisting of selected from the group consisting of HLA-DR+CD8+ T cells, CD26- CD8+ T cells, CD26+ CD8+ T cells, CD38- CD8+ T cells, CD32+ neutrophils, B cells, and natural killer (NK) cells, wherein levels of increased HLA-DR+ CD8+ T cells, increased CD26- CD8+ T cells, decreased CD26+ CD8+ T cells, increased CD38- CD8+ T cells, decreased CD32+ neutrophils, increased B cells, and increased natural killer (NK) cells, in the sample from the first individual in comparison to the control sample from the second individual or population of individuals is indicative of an autism spectrum disorder.

4. The method of claim 2, further comprising determining the level of one or more immune cell markers selected from the group consisting of selected from the group consisting of HLA-DR+CD8+ T cells, CD26- CD8+ T cells, CD26+ CD8+ T cells, CD38- CD8+ T cells, CD32+ neutrophils, B cells, and natural killer (NK) cells, wherein levels of increased HLA-DR+ CD8+ T cells, increased CD26- CD8+ T cells, decreased CD26+ CD8+ T cells, increased CD38- CD8+ T cells, decreased CD32+ neutrophils, increased B cells, and increased natural killer (NK) cells, in the sample from the first individual in comparison to the control sample from the second individual or population of individuals is indicative of an autism spectrum disorder.

5. The method of claim 1, wherein the sample is serum.

6. The method of claim 1, wherein the sample is blood.

7. The method of claim 1, wherein the autism spectrum disorder is high functioning autism.

8. The method of claim 1, wherein the autism spectrum disorder is low functioning autism.

9. The method of claim 1, wherein the individual suspected of having an autism spectrum disorder has a familial history of autoimmune disease.

10. The method of claim 1, wherein the level of the complement factor H-related protein (FHR1) is determined by mass spectrometry.

11. The method of claim 1, wherein the level of the complement factor H-related protein (FHR1) is determined by immunoassay.

12. The method of claim 2, wherein the level of the one or more polypeptide markers is determined by mass spectrometry.

13. The method of claim 2, wherein the level of the one or more polypeptide markers is determined by immunoassay.

14. The method of claim 3, wherein the level of the one or more immune cell markers is determined by flow cytometry.

15. The method of claim 4, wherein the level of the one or more immune cell markers is determined by flow cytometry.

* * * * *

UNITED STATES PATENT AND TRADEMARK OFFICE
CERTIFICATE OF CORRECTION

PATENT NO. : 7,604,948 B2 Page 1 of 1
APPLICATION NO. : 11/381976
DATED : October 20, 2009
INVENTOR(S) : Amaral et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 453 days.

Signed and Sealed this

Fourteenth Day of December, 2010

David J. Kappos
*Director of the United States Patent and Trademark Office*

SEQUENCE LISTING

<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: human TNF-alpha converting enzyme (TACE), ADAM
      metallopeptidase domain 17, snake venom-like protease (cSVP),
      CD156b peptide or breast cancer 1, early onset (BRCA1, BRCAI,
      BRCC1), breast and ovarian cancer susceptibility protein 1, IRIS,
      PSCP, RNF53 peptide

<400> SEQUENCE: 1

Met Leu Val Tyr Lys
 1               5

<210> SEQ ID NO 2
<211> LENGTH: 10
<212> TYPE: PRT
<213> ORGANISM: Artificial Sequence
<220> FEATURE:
<223> OTHER INFORMATION: human complement factor H-related protein 1
      precursor (FHR-1, CFHL1), H factor-like protein 1 (HFL1), H36
      peptide

<400> SEQUENCE: 2

Thr Gly Glu Ser Ala Glu Phe Val Cys Lys
 1               5                  10

<210> SEQ ID NO 3
<211> LENGTH: 21
<212> TYPE: PRT
<213> ORGANISM: Artificial Sequence
<220> FEATURE:
<223> OTHER INFORMATION: human complement component 3 (C3) beta chain
      precursor, acylation-stimulating protein cleavage
      product (ASP), ARMD9, CPAMD1 peptide

<400> SEQUENCE: 3

Lys Gly Tyr Thr Gln Gln Leu Ala Phe Arg Gln Pro Ser Ser Ala Phe
 1               5                  10                  15

Ala Ala Phe Val Lys
            20

<210> SEQ ID NO 4
<211> LENGTH: 11
<212> TYPE: PRT
<213> ORGANISM: Artificial Sequence
<220> FEATURE:
<223> OTHER INFORMATION: human apolipoprotein B-100 (ApoB-100) precursor
      peptide

<400> SEQUENCE: 4

Ser Glu Ile Leu Ala His Trp Ser Pro Ala Lys
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: human complement factor H-related protein 1
      precursor (FHR-1, CFHL1), H factor-like protein 1
      (HFL1), H36 peptide

```
<400> SEQUENCE: 5

Ile Thr Cys Thr Glu Glu Gly Trp Ser Pro Thr Pro Lys
1               5                   10

<210> SEQ ID NO 6
<211> LENGTH: 18
<212> TYPE: PRT
<213> ORGANISM: Artificial Sequence
<220> FEATURE:
<223> OTHER INFORMATION: human complement C1q subcomponent subunit C
      chain precursor (C1QC, C1QG) peptide

<400> SEQUENCE: 6

Phe Asn Ala Val Leu Thr Asn Pro Gln Gly Asp Tyr Asp Thr Ser Thr
1               5                   10                  15

Gly Lys

<210> SEQ ID NO 7
<211> LENGTH: 16
<212> TYPE: PRT
<213> ORGANISM: Artificial Sequence
<220> FEATURE:
<223> OTHER INFORMATION: human fibronectin 1 isoform 1 preproprotein,
      fibronectin 1 isoform 3 preproprotein (FN1, FN),
      cold-insoluble globulin (CIG), migration-stimulating
      factor (MSF), FINC, LETS peptide

<400> SEQUENCE: 7

Asn Leu Gln Pro Ala Ser Glu Tyr Thr Val Ser Leu Val Ala Ile Lys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: human complement component 4B alpha chain
      preproprotein (C4b, C4B, CH, C4F, CO4, C4B1,
      C4B1a, C4B2, C4B3, C4A12, C4A2, C4A91), Chido form
      of C4, basic C4, C4A anaphylatoxin, CPAMD3 peptide

<400> SEQUENCE: 8

Glu Pro Phe Leu Ser Cys Cys Gln Phe Ala Glu Ser Leu Arg
1               5                   10

<210> SEQ ID NO 9
<211> LENGTH: 13
<212> TYPE: PRT
<213> ORGANISM: Artificial Sequence
<220> FEATURE:
<223> OTHER INFORMATION: human mitotic-arrest deficient 1, yeast,
      homolog-like 1 (MAD1-like 1, MAD1L1), tumor
      protein p53 inducible protein 9 (TP53I9),
      tax1-binding protein (TXBP181), PIG9 peptide

<400> SEQUENCE: 9

Val Leu His Met Ser Leu Asn Pro Thr Ser Val Ala Arg
1               5                   10

<210> SEQ ID NO 10
<211> LENGTH: 18
<212> TYPE: PRT
<213> ORGANISM: Artificial Sequence
<220> FEATURE:
<223> OTHER INFORMATION: human apolipoprotein B-100 (ApoB-100) precursor
      peptide
```

```
<400> SEQUENCE: 10

Ile His Ser Gly Ser Phe Gln Ser Gln Val Glu Leu Ser Asn Asp Gln
1               5                   10                  15

Glu Lys

<210> SEQ ID NO 11
<211> LENGTH: 9
<212> TYPE: PRT
<213> ORGANISM: Artificial Sequence
<220> FEATURE:
<223> OTHER INFORMATION: human apolipoprotein A-IV precursor (apoA-IV,
      APOA4) peptide

<400> SEQUENCE: 11

Leu Ala Pro Leu Ala Glu Asp Val Arg
1               5

<210> SEQ ID NO 12
<211> LENGTH: 8
<212> TYPE: PRT
<213> ORGANISM: Artificial Sequence
<220> FEATURE:
<223> OTHER INFORMATION: human cytomatrix protein p110 (Spc110,
      SPBC110), ELKS/RAB6-interacting/CAST family member 2 (ERC2),
      CAZ-associated structural protein (CAST, CAST1) peptide

<400> SEQUENCE: 12

Glu Ser Ser Leu Ile Asp Leu Lys
1               5

<210> SEQ ID NO 13
<211> LENGTH: 9
<212> TYPE: PRT
<213> ORGANISM: Artificial Sequence
<220> FEATURE:
<223> OTHER INFORMATION: human Apolipoprotein C-II precursor (Apo-CII,
      ApoC-II, APOC2, APC2) peptide

<400> SEQUENCE: 13

Thr Tyr Leu Pro Ala Val Asp Glu Lys
1               5

<210> SEQ ID NO 14
<211> LENGTH: 8
<212> TYPE: PRT
<213> ORGANISM: Artificial Sequence
<220> FEATURE:
<223> OTHER INFORMATION: human Wnt-9a protein precursor (WNT9A), Wnt-14
      protein (WNT14) peptide

<400> SEQUENCE: 14

Trp Asn Cys Thr Leu Glu Gly Arg
1               5

<210> SEQ ID NO 15
<211> LENGTH: 17
<212> TYPE: PRT
<213> ORGANISM: Artificial Sequence
<220> FEATURE:
<223> OTHER INFORMATION: human WD repeat domain 17 isoform 1 (WDR17)
      peptide

<400> SEQUENCE: 15

Asn Glu Leu Leu Ile Leu Cys Gly Tyr Ile Gly Ala Leu Leu Ala Ile
1               5                   10                  15

Arg
```

```
<210> SEQ ID NO 16
<211> LENGTH: 16
<212> TYPE: PRT
<213> ORGANISM: Artificial Sequence
<220> FEATURE:
<223> OTHER INFORMATION: human apolipoprotein B-100 (ApoB-100) precursor
      peptide

<400> SEQUENCE: 16

Gly Ile Ile Ser Ala Leu Leu Val Pro Pro Glu Thr Glu Glu Ala Lys
 1               5                  10                  15

<210> SEQ ID NO 17
<211> LENGTH: 19
<212> TYPE: PRT
<213> ORGANISM: Artificial Sequence
<220> FEATURE:
<223> OTHER INFORMATION: human transferrin (TF) peptide

<400> SEQUENCE: 17

Ser Asp Asn Cys Glu Asp Thr Pro Glu Ala Gly Tyr Phe Ala Val Ala
 1               5                  10                  15

Val Val Lys

<210> SEQ ID NO 18
<211> LENGTH: 7
<212> TYPE: PRT
<213> ORGANISM: Artificial Sequence
<220> FEATURE:
<223> OTHER INFORMATION: human cdc2-related kinase PSSALRE conserved
      motif

<400> SEQUENCE: 18

Pro Ser Ser Ala Leu Arg Glu
 1               5
```